US010182735B2

(12) United States Patent
Thakur et al.

(10) Patent No.: US 10,182,735 B2
(45) Date of Patent: Jan. 22, 2019

(54) SYSTEMS AND METHODS FOR DETECTING ATRIAL TACHYARRHYTHMIA USING HEART SOUNDS

(71) Applicant: Cardiac Pacemakers, Inc., St. Paul, MN (US)

(72) Inventors: Pramodsingh Hirasingh Thakur, Woodbury, MN (US); Bin Mi, Plymouth, MN (US); Howard D. Simms, Jr., Shoreview, MN (US); Qi An, Blaine, MN (US); John D. Hatlestad, Maplewood, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/335,873

(22) Filed: Oct. 27, 2016

(65) Prior Publication Data

US 2017/0119273 A1     May 4, 2017

Related U.S. Application Data

(60) Provisional application No. 62/248,004, filed on Oct. 29, 2015.

(51) Int. Cl.
    *A61B 5/04*               (2006.01)
    *A61B 5/0464*           (2006.01)
    (Continued)

(52) U.S. Cl.
    CPC .......... *A61B 5/0464* (2013.01); *A61B 5/0205* (2013.01); *A61B 5/0245* (2013.01);
    (Continued)

(58) Field of Classification Search
None
See application file for complete search history.

(56) References Cited

U.S. PATENT DOCUMENTS 7,884,727 B2    2/2011   Tran
8,034,000 B2   10/2011   Zhang et al.
(Continued)

FOREIGN PATENT DOCUMENTS

WO    WO-2017075160 A1    5/2017

OTHER PUBLICATIONS

Go, Alan, et al., "Prevalence of Diagnosed Atrial Fibrillation in Adults: National Implications for Rhythm Management arid Stroke Prevention: the AnTicoagulation and Risk Factors in Atrial Fibrillation (ATRIA) Study", JAMA, 285(18), (2001), 2370-2375.
(Continued)

*Primary Examiner* — Ankit D Tejani
(74) *Attorney, Agent, or Firm* — Schwegman Lundberg & Woessner, P.A.

(57) ABSTRACT

Systems and methods for detecting atrial tachyarrhythmias (AT) such as atrial fibrillation (AF) are disclosed. A medical system can include a cardiac signal sensor circuit to sense a cardiac electrical signal and a heart sound (HS) sensor to sense heart a HS signal. A cardiac electrical signal metric, including a cycle length variability or a detection of atrial electrical activity, can be generated from the cardiac electrical signal. A HS metric can be generated from the HS signal, including a status of detection of S4 heart sound or a S4 heart sound intensity indicator. The system can include an AT detector circuit that can detect an AT event, such as an AF event, using the cardiac electrical signal metric and the HS metric. The system can additionally classify the detected AT event as an AF or an atrial flutter event.

20 Claims, 9 Drawing Sheets

(51) Int. Cl.
*A61B 5/024* (2006.01)
*A61B 5/0245* (2006.01)
*A61B 5/046* (2006.01)
*A61B 5/0205* (2006.01)
*A61B 5/00* (2006.01)
*A61B 7/02* (2006.01)
*A61B 5/11* (2006.01)

(52) U.S. Cl.
CPC .......... *A61B 5/02405* (2013.01); *A61B 5/046* (2013.01); *A61B 5/04012* (2013.01); *A61B 5/4836* (2013.01); *A61B 5/7275* (2013.01); *A61B 7/02* (2013.01); *A61B 5/1116* (2013.01); *A61B 5/1118* (2013.01); *A61B 5/686* (2013.01)

(56) References Cited

U.S. PATENT DOCUMENTS

| | | | |
|---|---|---|---|
| 9,332,924 | B2 | 5/2016 | Thakur et al. |
| 2006/0106322 | A1 | 5/2006 | Arand et al. |
| 2009/0306486 | A1 | 12/2009 | Li et al. |
| 2013/0237872 | A1 | 9/2013 | Zhang et al. |
| 2014/0296726 | A1* | 10/2014 | Brockway ............... A61B 7/00 600/514 |
| 2015/0106020 | A1* | 4/2015 | Chung .................. G16H 50/30 702/19 |
| 2015/0238147 | A1* | 8/2015 | Figgatt ............... A61B 5/04023 600/513 |

OTHER PUBLICATIONS

Heeringa, J., et al., "Prevalence, incidence and lifetime risk of atrial fibrillation: the Rotterdam study", Eur Heart Journal (8), (2006), 949-953.

Hindricks, G., et al., "Atrial Fibrillation Detection by a Subcutaneous Monitoring Device", Computers in Cardiology 2008;35, (2008), 413-416.

Kannel, WB, et al., "Final Draft Status of the Epidemiology of Atrial Fibrillation", Med Clin North Am. Jan. 2008 ; 92(1), (Jan. 2008), 1-25

Pürerfellner, H., et al., "P-wave evidence as a method for improving algorithm to detect atrial fibrillation in insertable cardiac monitors", Heart Rhythm; vol. 11, Issue 9, (Sep. 2014), 1575-1583.

"International Application Serial No. PCT/US2016/059031, Written Opinion dated Jan. 19, 2017", 5 pgs.

"International Application Serial No. PCT/US2016/059031, International Preliminary Report on Patentability dated May 11, 2018", 7 pgs.

"International Application Serial No. PCT/US2016/059031, International Search Report dated Jan. 19, 2017", 4 pgs.

"International Application Serial No. PCT/US20161059031, Written Opinion dated Jan. 19, 2017", 5 pgs.

* cited by examiner

SYSTEMS AND METHODS FOR DETECTING ATRIAL TACHYARRHYTHMIA USING HEART SOUNDS

CLAIM OF PRIORITY

This application claims the benefit of priority under 35 U.S.C. § 119(e) of U.S. Provisional Patent Application Ser. No. 62/248,004, filed on Oct. 29, 2015, which is herein incorporated by reference in its entirety.

TECHNICAL FIELD

This document relates generally to medical devices, and more particularly, to systems, devices and methods for detecting atrial tachyarrhythmia using heart sounds.

BACKGROUND

Cardiac arrhythmia is an abnormality in the timing or pattern of the heartbeat. Atrial tachyarrhythmia is a cardiac arrhythmia characterized by abnormally fast atrial rate, and can include various types of arrhythmias including atrial fibrillation, atrial flutter, atrial tachycardia, supraventricular tachycardia, among others. Atrial fibrillation (AF) is the most common clinical arrhythmia, and accounts for approximately one third of admissions resulting from cardiac rhythm disturbances. During AF, the normal regular sinus rhythm is overwhelmed by disorganized electrical pulses originated from regions in or near an atrium. This can lead to irregular conductions to ventricles, causing inappropriately fast and irregular heart rate. One type of AF is paroxysmal AF which may last from minutes to days before it stops by itself. Another type known as persistent AF may last for over a week and typically requires medication or other treatment to revert to normal sinus rhythm. The third type, permanent AF, is a condition where a normal heart rhythm cannot be restored with treatment. Persistent AF can become more frequent and result in permanent AF.

Congestive heart failure (CHF or HF) is another major cardiovascular epidemic and affects many people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood. CHF can affect the left heart, right heart or both sides of the heart, resulting in non-simultaneous contractions of the left ventricle and contractions of the right ventricle. Such non-simultaneous contractions, also known as dyssynchrony between the left and right ventricles, can further decrease the pumping efficiency of the heart.

There is a close pathophysiological relationship between AF and CHF. A large percentage of CHF patients may experience AF or other types of atrial tachyarrhythmias. AF may facilitate the development or progression of CHF, and CHF can increase the risk for the development of AF. The prevalence of AF in patients with CHF increased in parallel with the severity of CHF.

OVERVIEW

Atrial tachyarrhthmias (AT), such as AF, can coexist with HF in many CHF patients. AF may facilitate the development or progression of CHF in several ways. For example, during AF, irregularity of the ventricular contractions can result in reduction in left ventricular (LV) filling during short cycles which is not completely compensated for by increased filling during longer cycles. The loss of effective atrial contractile function also contributes to the deterioration of LV filling, particularly in CHF patients with diastolic dysfunction. Presence of untreated or uncontrolled AF may also reduce effectiveness of CHF therapies.

Timely and reliable detection of AF is necessary for treatment of AF and prevention of its exacerbating effect on CHF. Patients with AF frequently experience inappropriately rapid heart rate and irregular ventricular rhythm due to the loss of normal AV synchrony. As such, detection of an AF episode can be usually based on the fast atrial rate, or irregular ventricular contractions. However, atrial activity signal such as P wave in an electrocardiogram (ECG) can be a relatively weak signal compared to ventricular activity such as R wave or QRS complex which is produced by ventricular depolarization. Atrial activity signals can also be contaminated by noise, or interfered by various physiologic or environmental conditions. Although a dedicated atrial sensing such as by using an implanted lead placed in or near the atrium can improve atrial signal quality, it is not applicable to patient not indicated for atrial lead implantation. On the other hand, AF detection based on irregular ventricular contractions may suffer from confounding factors such as ventricular ectopic contracts or improper sensing of ventricular contractions, which may also manifest irregularity in R waves or QRS complexes. This can lead to reduced reliability of the detected ventricular contraction variability and false positive or false negative detections of AF. Therefore, the present inventors have recognized that there remains a considerable need of systems and methods that can reliably and accurately detect an AF episode.

Ambulatory medical devices (AMDs) can be used for monitoring HF patient and detecting HF worsening events. Examples of such ambulatory medical devices can include implantable medical devices (IMDs), subcutaneous medical devices, wearable medical devices or other external medical devices. Some AMDs can include a physiologic sensor that provides diagnostic features. One type of such physiologic sensor is a sensor for sensing heart sounds. Heart sounds are associated with mechanical vibrations from activity of a patient's heart and the flow of blood through the heart. Heart sounds recur with each cardiac cycle and are separated and classified according to the activity associated with the vibration. The first heart sound (S1) is associated with the vibrational sound made by the heart during tensing of the mitral valve. The second heart sound (S2) marks the beginning of diastole. The third heart sound (S3) can be related to filling pressures of the left ventricle during diastole. The fourth heart sound (S4) is associated with atrial contraction. The present inventors have recognized that, because atrial contraction may become diminished or irregular during an AF episode, a properly detected heart sound signal, such as S4 heart sound, can be used to improve the accuracy and reliability of detecting an AF episode.

Various embodiments described herein can help improve detection of an atrial tachyarrhythmia such as an AF episode, or improve the process of identifying patients at elevated risk of developing an AF episode. For example, a medical system can include a cardiac signal sensor circuit to sense a cardiac electrical signal and a heart sound (HS) sensor to sense heart a HS signal. A cardiac electrical signal metric, including a cycle length variability or a detection of atrial electrical activity, can be generated from the cardiac electrical signal. A HS metric can be generated from the HS signal, including a status of detection of S4 heart sound or a S4 heart sound intensity indicator. The system can include an AT detector circuit that can detect an AF event using the cardiac electrical signal metric and the HS metric.

In Example 1, a system can comprise a first sensor circuit and a second sensor circuit, a memory circuit, a first signal metric generator circuit, a second signal metric generator circuit, and an atrial tachyarrhythmia (AT) detector circuit. The first sensor circuit can include a sense amplifier circuit to sense a cardiac electrical signal of a patient, and the second sensor circuit can include a sense amplifier circuit to sense a heart sound (HS) signal of the patient. The first signal metric generator circuit can be coupled to the first sensor circuit and the memory circuit to detect from the cardiac electrical signal at least one signal component, and generate a cardiac electrical signal metric using the at least one signal component. The cardiac electrical signal metric can be stored in the memory circuit and indicative or correlative of atrial electrical activity. The second signal metric generator circuit can be coupled to the second signal sensor circuit and the memory circuit to detect from the HS signal at least one HS component including S4 heart sound, and generate a HS metric using the at least one HS component. The HS metric can be stored in the memory circuit and indicative or correlative of atrial mechanical contraction. The AT detector circuit can be communicatively coupled to the first and second signal metric generator circuits to detect an AT event using the cardiac electrical signal metric and the HS metric.

Example 2 can include, or can optionally be combined with the subject matter of Example 1 to optionally include, the AT detector circuit configured to detect an atrial fibrillation (AF) event. The first signal metric generator circuit can determine a cardiac cycle length (CL) or a heart rate (HR) from the cardiac electrical signal, and generate the cardiac electrical signal metric including a cycle length variability (CLV) of the CL or HR. The first signal metric can additionally or alternatively detect an atrial electrical activation from the cardiac electrical signal, and generate the cardiac electrical signal metric including an amplitude of the detected atrial electrical activation. The second signal metric generator circuit can detect the S4 heart sound within a cardiac cycle, and generate a S4 detection status indicating whether a S4 heart sound is detected within the cardiac cycle, or an S4 intensity indicator indicative of intensity of the detected S4 heart sound.

Example 3 can include, or can optionally be combined with the subject matter of Example 2 to optionally include a first comparator circuit, a second comparator circuit and a blending circuit. The first comparator circuit can compare the CLV value to a CLV threshold ($CLV_{TH}$). The second comparator circuit can compare the S4 intensity indicator of the detected S4 heart sound to a S4 intensity threshold ($\|S4\|_{TH}$). The blending circuit can detect the AF event if (1) the CLV value exceeds the $CLV_{TH}$, and (2) the S4 detection status indicates a non-detection of S4 heart sound, or the S4 intensity indicator falls below the $\|S4\|_{TH}$.

Example 4 can include, or can optionally be combined with the subject matter of Example 2 to optionally include a first counter circuit, a second counter circuit, and a blending circuit. The first counter circuit can determine a first relative number of a first subset of a plurality of CLV values computed over a plurality of cardiac cycles. Each CLV within the first subset exceeds a CLV threshold ($CLV_{TH}$). The second counter circuit can determine a second relative number of a second subset of the plurality of cardiac cycles. Each cardiac cycle within the second subset includes a detected S4 heart sound with a corresponding S4 intensity indicator exceeding a S4 intensity threshold ($\|S4\|_{TH}$). The blending circuit can generate a composite score using the first and second relative numbers, and detect the AF event if the composite score meets a specified criterion.

Example 5 can include, or can optionally be combined with the subject matter of Example 4 to optionally include, the blending circuit that can generate the composite score including a difference between the first relative number and the second relative number.

Example 6 can include, or can optionally be combined with the subject matter of Example 2 to optionally include, a beat selector circuit coupled to the second signal metric generator circuit. The beat selector circuit can select, from a plurality of cardiac cycles for detecting S4 heart sound, a subset of cardiac cycles each having the S4 detection status indicating non-detection of S4 heart sound within the corresponding cardiac cycle, or the S4 intensity indicator falling below a S4 intensity threshold. The first signal metric generator circuit can to compute the CLV value using the selected subset of the cardiac cycles. The AT detector circuit can detect the AF event if the CLV value exceeds a CLV threshold.

Example 7 can include, or can optionally be combined with the subject matter of Example 2 to optionally include, a beat selector circuit coupled to the first signal metric generator circuit. The beat selector circuit can select from a plurality of cardiac cycles a subset of cardiac cycles corresponding to the CLV exceeding a CLV threshold. The second signal metric generator circuit is configured to detect S4 heart sounds within the selected subset of the cardiac cycles and generate a S4 detection status. The AT detector circuit can detect the AF event if the S4 detection status indicating non-detection of S4 heart sound within the selected subset of the cardiac cycles, or the S4 intensity indicator falling below a S4 intensity threshold.

Example 8 can include, or can optionally be combined with the subject matter of Example 2 to optionally include, an activity sensor circuit that can detect a physical activity level of the patient. The AT detector circuit can detect the AF event using the detected atrial electrical activation if the detected physical activity level exceeds a specified activity threshold, or detect the AF event using the detected S4 heart sound if the detected physical activity level falls below the specified activity threshold.

Example 9 can include, or can optionally be combined with the subject matter of Example 2 to optionally include, a posture sensor circuit that can detect a posture of the patient. The AT detector circuit can detect the AF event using the detected atrial electrical activation if the detected posture is a first posture, or detect the AF event using the detected S4 heart sound if the detected posture is a different second posture.

Example 10 can include, or can optionally be combined with the subject matter of Example 2 to optionally include, the first signal metric generator circuit that can detect from the cardiac electrical signal the atrial electrical activation and the CL or the HR, and generate the cardiac electrical signal metric including the CLV. The AT detector circuit can detect the AF event if the CLV value exceeds a CLV threshold ($CLV_{TH}$). The $CLV_{TH}$ can be determined using one or both of the detection of the S4 heart sound and the detection of the atrial electrical activation.

Example 11 can include, or can optionally be combined with the subject matter of Example 10 to optionally include, the AT detector circuit that can determine a first CLV threshold ($CLV_{TH1}$) in response to both of a detection of S4 heart sound and a detection of atrial electrical activation, a second CLV threshold ($CLV_{TH2}$) in response to one of a detection of S4 heart sound or a detection of atrial electrical activation, or a third CLV threshold ($CLV_{TH3}$) in response to neither a detection of S4 heart sound nor a detection of atrial electrical activation. The threshold $CLV_{TH1}$ can be greater than the $CLV_{TH2}$, and the $CLV_{TH2}$ can be greater than the $CLV_{TH3}$.

Example 12 can include, or can optionally be combined with the subject matter of Example 10 to optionally include, the AT detector circuit than can determine a first CLV threshold ($CLV_{TH1}$) in response to the detection of S4 heart sound, a second ON threshold ($CLV_{TH2}$) in response to the detection of atrial electrical activation, or a third CLV threshold ($CLV_{TH3}$) in response to neither a detection of S4 heart sound nor a detection of atrial electrical activation. The threshold $CLV_{TH1}$ can be different from the $CLV_{TH2}$, and the $CLV_{TH3}$ can be less than $CLV_{TH1}$ and less than $CLV_{TH2}$.

Example 13 can include, or can optionally be combined with the subject matter of one or any combination of Examples 1 through 12 to include, an arrhythmia classifier circuit coupled to the memory circuit or the first and second signal metric generator circuits. The arrhythmia classifier circuit can determine a composite metric using the cardiac electrical signal metric and the HS metric, and confirm the detected AT event as an AF event if the composite metric meets a first specified criterion, or classify the detected AT event as an atrial flutter (AFL) event if the composite metric meets a second specified criterion.

Example 14 can include, or can optionally be combined with the subject matter of Example 13 to optionally include, the composite metric including a variability ($AVR_{var}$) of an atrio-ventricular conduction pattern including a ratio (AVR) of a number of S4 heart sounds to a number of ventricular activations during a specified number of cardiac cycles. The arrhythmia classifier circuit can confirm the detected AT event as an AF event if the $AVR_{var}$ exceeds a specified threshold, or classify the detected AT event as an AFL event if the AVRvar falls below the specified threshold.

Example 15 can include, or can optionally be combined with the subject matter of Example 13 to optionally include, the composite metric including a variability ($AVI_{var}$) of atrio-ventricular interval including an interval between the detected S4 heart sound and the ventricular activation within the same cardiac cycle. The arrhythmia classifier circuit can confirm the detected AT event as an AF event if the $AVI_{var}$ exceeds a specified threshold, or classify the detected AT event as an AFL event if the $AVI_{var}$ falls below the specified threshold.

In Example 16, a method can include steps of sensing a cardiac electrical signal of a patient, generating front the sensed cardiac electrical signal a cardiac electrical signal metric indicative or correlative of atrial electrical activity, sensing a heart sound (HS) signal of the patient generating from the sensed HS signal a HS metric indicative or correlative of atrial mechanical contraction, the HS metric including a S4 heart sound metric, and detecting an atrial tachyarrhythmia (AT) event using the cardiac electrical signal metric and the HS metric.

Example 17 can include, or can optionally be combined with the subject matter of Example 16 to optionally include, generating the cardiac electrical signal metric including one or more of a cycle length variability (CLV) of cycle length (CL) or HR computed from the cardiac electrical signal or an atrial electrical activation detected from the cardiac electrical signal, and generating the HS metric including one or more of a S4 detection status indicating whether a S4 heart sound is detected within the cardiac cycle, or a S4 intensity indicator of the detected S4 heart sound. Example 17 can include detecting the AT event includes detecting an atrial fibrillation (AF) event if (1) the CLV value exceeds a CLV threshold ($CLV_{TH}$), and (2) the S4 detection status indicates a non-detection of S4 heart sound, or the S4 intensity indicator falls below a S4 intensity threshold ($\|S4\|_{TH}$).

Example 18 can include, or can optionally be combined with the subject matter of Example 17 to optionally include, determining a first relative number of a first subset of a plurality of CLV values computed over a plurality of cardiac cycles, each CLV within the first subset exceeding the $CLV_{TH}$, and a second relative number of a second subset of the plurality of cardiac cycles each including a detected S4 heart sound with a corresponding S4 intensity indicator exceeding the $\|S4\|_{TH}$. Example 18 can including generating a composite score using the first and second relative numbers, and detecting the AF event if the composite score meets a specified criterion.

Example 19 can include, or can optionally be combined with the subject matter of Example 17 to optionally include, selecting from a plurality of cardiac cycles for detecting S4 heart sound a subset of cardiac cycles each having the S4 detection status indicating non-detection of S4 heart sound within the corresponding cardiac cycle, or the S4 intensity indicator falling below the $\|S4\|_{TH}$. Example 19 can include generating the CLV value using the selected subset of the cardiac cycles, and detecting the AF event if the CLV value exceeds the $CLV_{TH}$.

Example 20 can include, or can optionally be combined with the subject matter of Example 17 to optionally include, detecting at least one of a physical activity level or a posture of the patient, and detecting the AF event using the detected atrial electrical activation if the detected physical activity level exceeds a specified activity threshold or the detected posture is a first posture, or detecting the AF event using the detected S4 heart sound if the detected physical activity level falls below the specified activity threshold or the detected posture is a different second posture.

Example 21 can include, or can optionally be combined with the subject matter of Example 17 to optionally include, determining the $CLV_{TH}$ using one or both of the detection of the S4 heart sound and the detection of the atrial electrical activation. The $CLV_{TH}$ can be a first CLV threshold ($CLV_{TH1}$) in response to both of a detection of S4 heart sound and a detection of atrial electrical activation, a second CLV threshold ($CLV_{TH2}$) in response to one of a detection of S4 heart sound or a detection of atrial electrical activation, or a third CLV threshold ($CLV_{TH3}$) in response to neither a detection of S4 heart sound nor a detection of atrial electrical activation. The $CLV_{TH1}$ can be greater than the $CLV_{TH2}$, and the $CLV_{TH2}$ can be greater than the $CLV_{TH3}$. Example 21 can include detecting the AF event if the CLV value exceeds the $CLV_{TH}$.

Example 22 can include, or can optionally be combined with the subject matter of Example 16 to optionally include, classifying the detected AT event as one of an atrial fibrillation (AF) event or an atrial flutter (AFL) event. A composite metric can be computed using the cardiac electrical signal metric and the HS metric, the composite metric can include one of more of an atrio-ventricular conduction pattern or an atrio-ventricular interval. The classification can include confirming the detected AT event as an AF event if the composite metric meets a first specified criterion indicating a consistent atrio-ventricular conduction pattern or a stable atrio-ventricular interval, or classifying the detected AT event as an AFL event if the composite metric meets a second specified criterion indicating an inconsistent atrio-ventricular conduction pattern or an unstable atrio-ventricular interval.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting atrial tachyarrhythmias such as atrial fibrillation (AF). By monitoring a patient's cardiac electrical activity and a heart sound (HS) signal, the system and methods discussed in the present document can be used to timely and reliably detect an AF episode, thereby allowing immediate medical attention to the patient. The systems and methods discussed in this document can also be used for detecting other types of atrial tachyarrhythmias such atrial tachycardia, atrial flutter, or supraventricular tachycardia.

Figure 1:
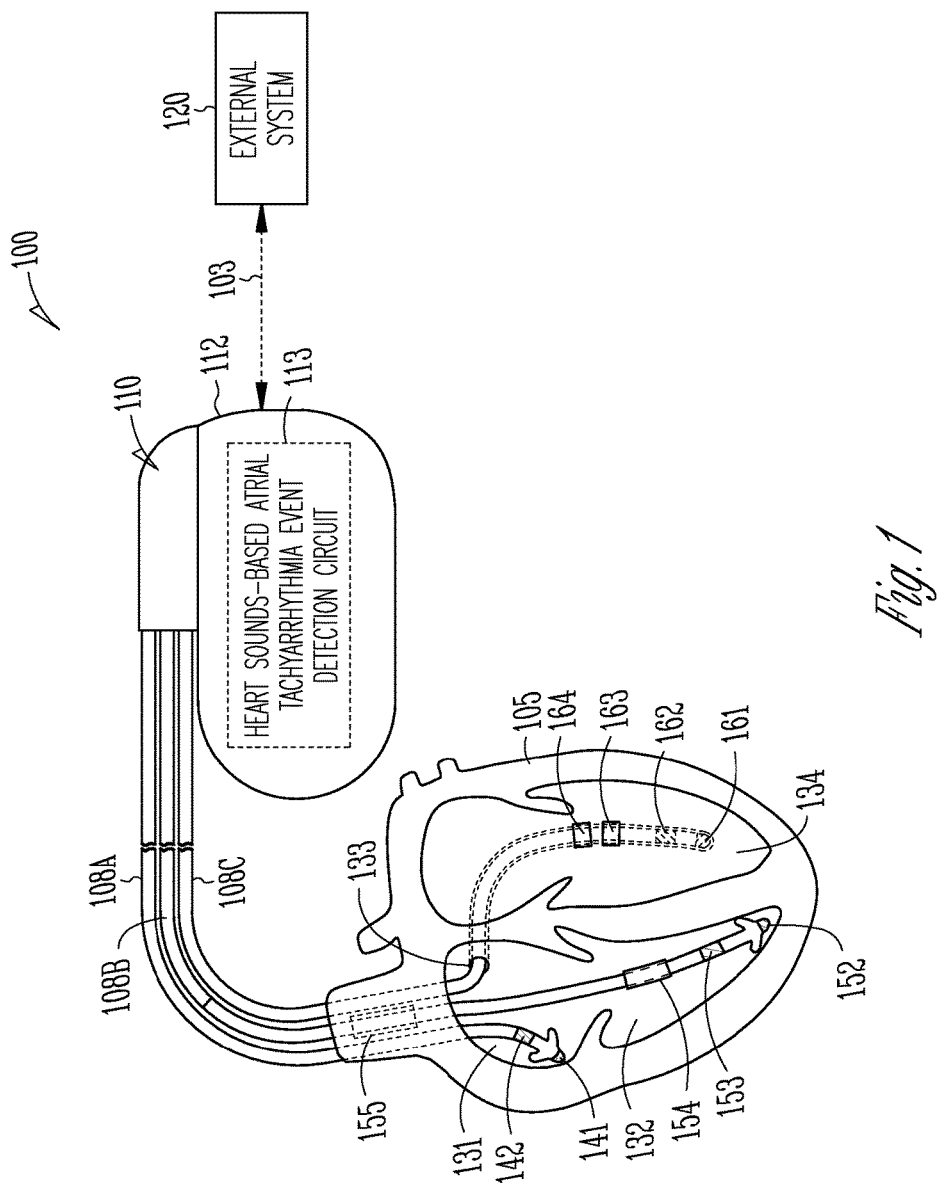
FIG. 1 illustrates generally an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a heart sounds-based atrial tachyarrhythmia (AT) event detection circuit 113. The heart sounds-based AT event detection circuit 113 can be configured to detect a heart sound (HS) signal such as by using an implantable sensor, and produce a HS metric indicative or correlative of atrial mechanical contraction. The heart sounds-based AT event detection circuit 113 can additionally detect a cardiac electrical signal and generate a signal metric indicative or correlative of atrial electrical activity. The heart sounds-based AT event detection circuit 113 can combine the signal metrics indicative of atrial electrical activity and the signal metrics indicative of atrial mechanical contraction to detect an AT event, such as a atrial (AF) event. Examples of heart sounds-based AT event detection circuit 113 are described below, such as with reference to FIGS. 2-3.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The heart sounds-based AT event detection circuit 113 can be implemented at the external system 120 such as using data extracted from the IMD 110 or data stored in a memory within the external system 120. Portions of the heart sounds-based AT event detection circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

While described with reference to the IMD 110, the CRM system 100 can include a subcutaneous medical device (e.g., subcutaneous pacemaker or ICD, a subcutaneous monitor, or a subcutaneous diagnostic device), a wearable medical device (e.g., a patch based sensing device), or other external medical devices for medical diagnostics or therapy using various energy sources (e.g., electrical, electromagnetic, optical, or mechanical) or therapeutic agents. The subcutaneous, wearable, or external medical device can be an untethered device that needs not be tethered to an electrode or another device by a leadwire or other wired connection (such as one of the leads 108A-C). The untethered device can include one or more electrodes on a can housing of the device, or wirelessly communicate with a sensor or another device associated with the patient.

Figure 2:
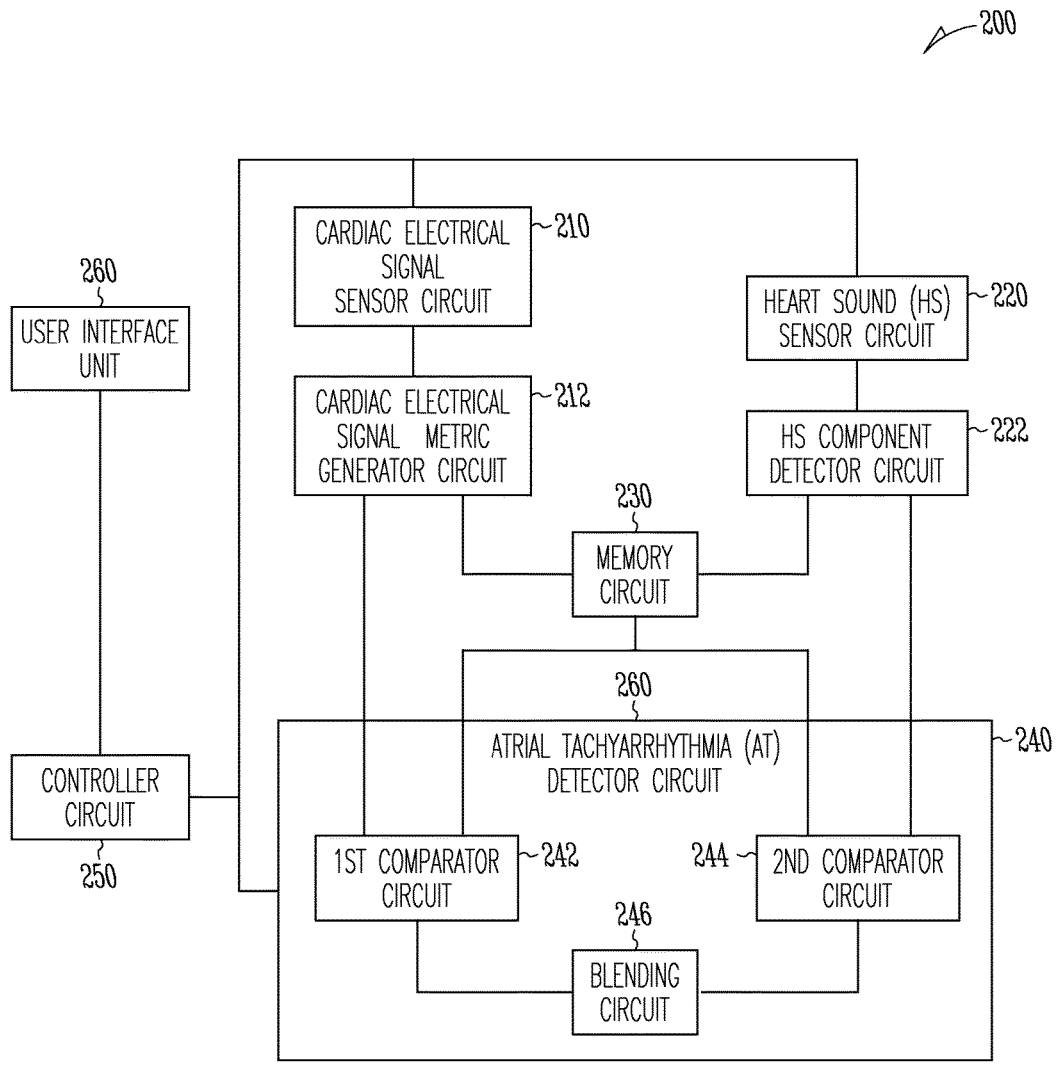
FIG. 2 illustrates generally an example of a HS-based atrial tachyarrhythmia (AT) detection circuit.

FIG. 2 illustrates an example of a heart sound (HS)-based atrial tachyarrhythmia (AT) detection circuit 200, which can be an embodiment of the heart sounds-based AT event detection circuit 113. The HS-based AT detection circuit 200 can alternatively be implemented in an external system such as a patient monitor configured for providing diagnostic information to an end-user. The HS-based AT detection circuit 200 can include one or more of a cardiac electrical signal sensor circuit 210, a HS sensor circuit 220, a cardiac electrical signal metric generator circuit a HS metric generator circuit 222, a memory circuit 230, an AT detector circuit 240, a controller circuit 250, and a user interface unit 250.

The cardiac electrical signal sensor circuit 210 can sense a cardiac electrical signal from a patient. The cardiac electrical signal sensor circuit 210 can include one or more implantable, wearable, or otherwise ambulatory cardiac activity sensors configured to sense cardiac electrical activity. In an example, the cardiac activity sensor can include electrodes on one or more of the leads 108A-C or the can 112. The electrodes are configured for sensing one or more electrograms (EGMs) from inside the heart chamber, inside the heart tissue, on or near the surface of the heart. The electrodes can be non-invasively attached to the skin to sense a surface electrocardiogram (ECG). The electrodes can also placed subcutaneously (e.g., under the skin) to sense a subcutaneous ECG.

The cardiac electrical signal sensor circuit 210 can include one or more amplifiers, analog to digital converters, filters, or other signal conditioning circuits that can process the sensed cardiac electrical activity, such as an ECG, a subcutaneous ECG, or an EGM. The cardiac electrical signal sensor circuit 210 can detect from the processed cardiac electrical activity signals electrophysiological events such as events indicative of depolarization or repolarization of a specified portion of the heart, such as an atrium, a ventricle, a His-bundle, or a septum.

The cardiac electrical signal metric generator circuit 212 can be coupled to the cardiac electrical signal sensor circuit 210 to detect from the cardiac electrical signal at least one signal component, and generate a signal metric using the at least one signal component. In one example, the cardiac electrical signal sensor circuit 210 can sense ventricular depolarizations such as R waves or QRS complexes from the ECG signal, or ventricular sensing (Vs) events from the ventricular EGM such as by using at least one electrode on the RV lead 108B or the LV lead 108C. The cardiac electrical signal sensor circuit 210 can derive from the sensed ventricular depolarizations a heart rate (HR) or a cycle length (CL) signal. The CL can be determined as, for example, intervals between two adjacent R waves, and the HR can be computed using the CL. The cardiac electrical signal metric generator circuit 212 can generate the cardiac electrical signal metric including a cycle length variability (CLV) or a heart rate variability (HRV), which can be respectively computed as a spreadness measure over a plurality CLs or HRs. One example of the spreadness measure can include first-order statistics such as an average of beat-to-beat difference in HR or CL measurements, second-order statistics such as a variance or a standard deviation, or higher-order statistics of the or CL measurements. Another example of the spreadness measure can include geometric features extracted from a two dimensional scatter plot between two successive HR or CL measurements (e.g., CL(n) vs. CL(n−1)) or from a higher dimensional scatter plot among three or more HR or CL measurements (e.g., CL(n) vs. CL(n−1) vs. CL(n−2)).

In another example, the cardiac electrical signal sensor circuit 210 can sense atrial electrical activity, such as P waves from the ECG or atrial sensing events acquired using at least one atrial electrode on the atrial lead 108A. The cardiac electrical signal metric generator circuit 212 can generate the cardiac electrical signal metric including a presence or intensity of atrial depolarizations. The cardiac electrical signal metric, such as the CLV, HRV, or the presence or intensity of the atrial depolarizations such as the P waves, can be stored in the memory circuit 230.

The HS sensor circuit 220 can sense HS information indicative of acoustic or mechanical activity of a heart. The HS information can include information of at least one HS component, such as S1, S2, S3, or S4 heart sound. In an example, the HS waveform can include at least one ensemble average of a HS signal over multiple physiological cycles such as multiple cardiac cycles, or over a specified time period such as one minute, ten minutes, one hour, one day, etc.

The HS sensor circuit 220 can be coupled to one or more physiologic sensors that can be configured to sense, detect, or otherwise obtain HS information from a subject. Such physiologic sensors, hereinafter referred to as "HS sensors", can be an implantable, wearable, or otherwise ambulatory sensor, and placed external to the patient or implanted inside the body. Examples of the HS sensor can include an accelerometer, an acoustic sensor, a microphone, a piezo-based sensor, or other vibrational or acoustic sensors can also be used to sense the HS signal. The HS sensor can be included in at least one part of an implantable system, such as an implantable medical device, or a lead coupled to the implantable medical device. In an example, the signal sensor circuit 210 can be configured to receive the HS information from a device capable of collecting or storing the HS information. Examples of such a device can include an external programmer, an electronic medical record system, a memory unit, or other data storage devices.

The HS sensor circuit 220 can include a sense amplifier circuit that can pre-process a sensed HS signal, including amplification, digitization, filtering, or other signal conditioning operations. In an example, the signal sensor circuit 210 can include a bandpass filter adapted to filter the received HS signal to a frequency range of approximately between 5 and 90 Hz, or approximately between 9 and 90 Hz. In an example, the signal sensor circuit 210 can include a double or higher-order differentiator configured to calculate a double or higher-order differentiation of the received HS signal.

The HS metric generator circuit 222 can detect from the HS signal at least one HS component, and generate a HS metric indicative or correlative of atrial mechanical contraction using the at least one HS component. In an example, the HS metric generator circuit 222 can detect a S4 heart sound, among other heart sound components. The S4 heart sound may generally be associated with atrial contraction. During AF, regular and forceful atrial contraction may be diminished. As such, a detection of forceful S4 can be an evidence of absence of AF. The HS metric generator circuit 222 can detect S4 using a specified detection window, such as with reference to a physiologic event such as R wave, Q wave, or QRS complexes obtained from an electrocardiogram or an intracardiac electrogram signal synchronously sensed with the HS signal. The HS metric generator circuit 222 can detect S4 heart sound along with one or more other heart sounds such as S1, S2, or S3. In an example, because S4 generally occurs temporally following S3 and prior to S1 of the next cardiac cycle, the S4 detection window can be with reference to detected S1 or S3 heart sound. The HS metric generator circuit 222 can calculate HS signal energy within the S4 detection window, and detects the S4 if the HS signal energy exceeds a specified threshold. In an example, the HS metric generator circuit 222 can detect the HS component adaptively by tracking the temporal locations of the previously detected HS component. Additionally or alternatively, the HS metric generator circuit 222 can detect S4 heart sound using a S4 template matching method. A S4 morphological template can be created using the known S4 signal portion extracted from the patient's HS signal. A matching score, such as a cross correlation, between a segment of HS signal within a cardiac cycle and the S4 template can be computed. An S4 can be detected if the matching score exceeds a threshold value.

The HS metric generator circuit 222 can generate one or more HS metrics including a detection status of S4 heart sound, and temporal, statistical, or morphological features of the detected S4 heart sound. Examples of the intensity of a HS component can include amplitude of a detected HS component in a time-domain HS signal, a transformed HS signal such as integrated HS energy signal, or in a frequency-domain HS signal such as the peak value of the power spectral density, or peak value of a generic measurement within the respective HS detection window, such as peak envelop signal or root-mean-squared value of the portion of the HS signal within the HS detection window. The intensity of a HS component can also include a slope or rate of change of signal amplitude or peak energy. In an example, the HS metric can include an intensity measure of a portion of the HS signal that includes at least a portion of a specified HS component, such as a root-mean-squared value of the HS signal portion between an R wave and a subsequent S1 heart sound, or between an R wave and a subsequent S2 heart sound, within the same cardiac cycle. The HS metric, such as the detection of S4, or intensity or other features derived from the detected S4 heart sound, can be stored in the memory circuit 230.

The AT detector circuit 240 can be communicatively coupled to the memory circuit 230, or the cardiac electrical signal metric generator circuit 212 and the HS metric generator circuit 222. The AT detector circuit 240 can use one or more of the cardiac electrical signal metrics or the HS metrics to detect an AT event, such as an AF event. In an example, the AT detector circuit 240 can be implemented as a part of a microprocessor circuit in the CRM system 100. The microprocessor circuit can be a dedicated processor such as a digital signal processor, application specific integrated circuit (ASIC), microprocessor, or other type of processor for processing information including heart sounds. Alternatively, the microprocessor circuit can be a general purpose processor that can receive and execute a set of instructions of performing the functions, methods, or techniques described herein.

The AT detector circuit 240 can include a first comparator circuit 242, a second comparator circuit 244, and a blending circuit 246. The first comparator circuit 242 can compare the cardiac electrical signal metric to a specified criterion and produce an atrial rhythm indicator. In an example, the first comparator circuit 242 can compare the CLV value to a CLV threshold ($CLV_{TH}$), and produce an atrial rhythm indicator if the CLV value exceeds the $CLV_{TH}$. The second comparator circuit 244 can compare the HS metric to a specified criterion and produce an atrial kick indicator. In an example, if an S4 is detected by the HS metric generator circuit 222, the second comparator circuit 244 can compare the detected S4 intensity ($\|S4\|$) to a S4 intensity threshold ($\|S4\|_{TH}$), and produce the atrial kick indicator including an indication of a non-detection of S4 heart sound, or an indicator of the detected S4 intensity exceeding or falling below the $\|S4\|_{TH}$.

The blending circuit 246 can combine the atrial rhythm indicator and the atrial kick indicator to detect an AF event. In an example, an AF event is detected if (1) the CLV value exceeds the $CLV_{TH}$, and (2) the S4 heart sound is not detected, or the S4 intensity indicator falls below the $\|S4\|_{TH}$. In an example, the $CLV_{TH}$ can be set a relatively low level such that CLV can be sensitive to cycle length variations. The $\|S4\|_{TH}$ can be selected such that the atrial kick indicator, such as a non-detection of S4 or a below-the-threshold S4 intensity, can be specific to an AF event. In an example of using an accelerometer sensor to sense HS and detecting HS components (e.g., S4 heart sound) from root-mean-squared (RMS) values of the acceleration signal, the $\|S4\|_{TH}$ can be approximately 0.6 milli-G, as a non-limiting example.

In some examples, the first comparator circuit 242 can compare the CLV value to a distribution of CLV values to determine a first likelihood value of the CLV value indicative of an AF event. The CLV distribution can be determined during a period when the patient is free of AT, such as in a sinus rhythm, using population-based or patient historical cycle lengths or cardiac cycles. Similarly, the second comparator circuit 244 can compare the HS metric to a population-based or a patient-specific distribution of $\|S4\|$ to determine a second likelihood value of the $\|S4\|$ value indicative of an AF event. The $\|S4\|$ distribution can be determined when the patient is free of AT using population-based or patient historical HS data. The blending circuit 246 can generate a composite likelihood using the first and second likelihood values, and detect the AF event if the composite likelihood meets a specified criterion.

In an example, the cardiac electrical signal metric generator circuit 212 can generate a plurality of CLV values using a plurality of cardiac cycles. The HS metric generator circuit 222 can detect S4 heart sound within the plurality of cardiac cycle, and generate the S4 intensity indicator for the detected S4 heart sound. The first comparator circuit 242 can include a first counter circuit to determine a first relative number ($N_{CLV}$) of the plurality of CLV values that exceed a CLV threshold ($CLV_{TH}$). The second comparator circuit 244 can include a second counter circuit to determine a second relative number ($N_{S4}$) of the cardiac cycles within which a S4 heart sound is detected and the S4 intensity exceeds the S4 intensity threshold $\|S4\|_{TH}$. Examples of the relative numbers $N_{CLV}$ and $N_{S4}$ can include respective ratio, fraction, or percentage, among others. The blending circuit 246 can generate a composite score using the first relative number $N_{CLV}$ and the second relative number $N_{S4}$, and detect the AF event if the composite score meets a specified criterion. In an example, the $N_{CLV}$ can represent percentage of the plurality of cardiac cycles satisfying $CLV > CLV_{TH}$, and $N_{S4}$ can represent percentage of the plurality of cardiac cycles satisfying $\|S4\| > \|S4\|_{TH}$. The composite score can be computed as difference $N_{CLV} - N_{S4}$. Because a larger $N_{CLV}$ may indicate higher likelihood of occurrence of an AF event, and a larger $N_{S4}$ may indicate stronger evidence of forceful atrial contraction and thus lower likelihood of occurrence of an AF event, the difference ($N_{CLV} - N_{S4}$) can represent cumulative likelihood of occurrence of an AF event. In an example, the AT detector circuit 240 can detect an AF event if $N_{CLV} - N_{S4}$ exceeds a specified detection threshold. Other relative measures between $N_{CLV}$ and $N_{S4}$, such as weighted difference, can also be used.

In an example, detection of atrial kick (such as $\|S4\|$) can be used to screen and select cardiac cycles for use in determining the CLV. The second comparator circuit 244 can include a beat selector circuit, coupled to the HS component detector circuit 222, that can select, from a plurality of cardiac cycles used by the HS metric generator circuit 222 for detecting S4 heart sound, a subset of cardiac cycles each having a non-detection of S4 heart sound within the corresponding cardiac cycle, or the intensity of the detected S4 heart sound falling below the threshold $\|S4\|_{TH}$. The selected cardiac cycles thus represent time intervals free of forceful atrial kick, an indication of presence of an AF event. The cardiac electrical signal metric generator circuit 212 can use only the selected subset of the cardiac cycles to computed CLV values. The AT detector circuit 240 can detect the AF event if the CLV value exceeds a CLV threshold ($CLV_{TH}$). In another example, the beat selector circuit can select the subset of cardiac cycles using both the S4 heart sounds and atrial electrical activation, such as when there is no detection of S4 heart sound or $\|S4\|<\|S4\|_{TH}$, and there is no detected atrial electrical activation (e.g., no detectable P waves from the ECG). The beat selector circuit can alternatively be coupled to the cardiac electrical signal metric generator circuit 212, and can select from a plurality of cardiac cycles a subset of cardiac cycles corresponding to the CLV exceeding $CLV_{TH}$. The HS component detector circuit 222 can detect S4 heart sounds within the selected subset of the cardiac cycles and generate a S4 detection status. The AT detector circuit 240 can detect the AF event if the S4 detection status indicates non-detection of S4 heart sound within the selected subset of the cardiac cycles, or the S4 intensity indicator falling below the S4 intensity threshold $\|S4\|_{TH}$.

In some examples, detection of atrial kick or atrial electrical activation can be used to determine a CLV threshold ($CLV_{TH}$). The cardiac electrical signal metric generator circuit 212 can detect from the cardiac electrical signal the atrial electrical activation (such as P waves from the ECG signal or atrial sensing events from atrial EGM), and generate cardiac electrical signal metric of CLV using the CL or the HR. The AT detector circuit 240 can detect the AF event if the CLV value exceeds a CLV threshold ($CLV_{TH}$). Different values of the threshold $CLV_{TH}$ can be determined based on the detected atrial electrical activation (e.g., P waves or atrial sensing events) and the atrial kick indicator (e.g., detected S4 heart sound such that $\|S4\|>\|S4\|_{TH}$). In an example, a first CLV threshold ($CLV_{TH1}$) can be determined in response to both the following conditions are met: (1) the atrial kick indicator of $\|S4\|>\|S4\|_{TH}$; and (2) the detection of atrial electrical activation. A second threshold ($CLV_{TH2}$) can be generated in response to either, but not both, of the above conditions (1) or (2) is met. A third threshold ($CLV_{TH3}$) can be generated in response to neither the condition (1) nor the condition (2) is met. In an example, $CLV_{TH1}$ can be greater than $CLV_{TH2}$. In another example, $CLV_{TH2}$ can be greater than $CLV_{TH3}$. Detections of both a S4 heart sound with intensity $\|S4\|>\|S4\|_{TH}$ and atrial electrical action (e.g., detection of P waves) may provide stronger evidence of non-occurrence of AF event than if only one, but not both, of a S4 heart sound and atrial electrical activation are detected. Thus, a larger threshold value $CLV_{TH1}$ ($CLV_{TH1}>CLV_{TH2}$) may avoid false positive detection of AF event. In an example, $CLV_{TH1}$ can be set to a positive infinity, which equivalently allows the AT detector circuit 240 to detect an AF event as long as there are evidence of atrial electrical activation and strong atrial kick ($\|S4\|>\|S4\|_{TH}$). A non-detection of S4 (or $\|S4\|<\|S4\|_{TH}$) along with non-detectable atrial electrical activation (or intensity of atrial activation falling below a threshold) may be a strong indicator of presence of an AF event. Thus, a smaller $CLV_{TH3}$ ($CLV_{TH3}<CLV_{TH2}$) may avoid missing a detection of an AF event.

In some examples, atrial kick indicator may provide different levels of evidence about occurrence of an AF event than a detection of atrial electrical activation. For example, based on population data, empirical knowledge, or signal quality (such as a signal noise ratio, SNR), an S4 heart sound with $\|S4\|>\|S4\|_{TH}$ may indicate a higher likelihood of occurrence of an AF event than a detection of P waves from the ECG or atrial sensing events from the atrial EGM. The AT detector circuit 240 can determine a first CLV threshold ($CLV_{TH1}$) In response to the detection of $\|S4\|>\|S4\|_{TH}$, a second CLV threshold ($CLV_{TH2}$) in response to the detection of atrial electrical activation, or a third CLV threshold ($CLV_{TH3}$) in response to neither a detection of S4 heart sound nor a detection of atrial electrical activation. As previously discussed, non-detection of S4 coupled along with no detectable atrial electrical activation may strongly suggest occurrence of an AF event. Thus, the corresponding threshold $CLV_{TH3}$ can be smaller ($CLV_{TH3}<CLV_{TH1}$ and $CLV_{TH3}<CLV_{TH2}$) to avoid missing a detection of an AF event. Between $CLV_{TH1}$ and $CLV_{TH2}$, if it is determined from population data or empirical knowledge that presence of S4 is more predictive of non-occurrence of AF, or if S4 has a higher signal quality (e.g., a higher SNR) than that of the P waves or atrial sensing events, then $CLV_{TH1}$ can be greater than $CLV_{TH2}$. Conversely, if the detection of P waves or atrial sensing events is more predictive of non-occurrence of AF, or if the P waves or the atrial EGM has a higher SNR than the S4 heart sound, then $CLV_{TH1}$ can be smaller than $CLV_{TH2}$.

The controller circuit 250 can receive external programming input from the user interface unit 260 to control the operations of the cardiac electrical signal sensor circuit 210, the HS sensor circuit 220, the AT detector circuit 240, and the data flow and instructions between these components. The user interface unit 260 can include a display that presents programming options to the user and receive system user's programming input. In an example, at least a portion of the user interface circuit 260, such as the display and user input control, can be implemented in the external system 120.

The HS-based AT detection circuit 200 can optionally include a therapy delivery circuit that can provide and deliver therapy to the patient in response to detection of the AF event, or to withhold the therapy to the patient if the AF event is no longer detected. The therapy can include one or more of a cardiac stimulation therapy, a cardiac ablation therapy, a neurostimulation therapy, or pharmacological therapy, among other therapy modalities. In an example, the cardiac stimulation therapy can be in a form of electrostimulation to a target tissue inside or on the heart, including an endocardium or an epicedium of an atrium or a ventricle. The electrostimulation can be delivered via one or more of the leads 108A-C or the can 112. Examples of electrostimulation therapy can include ventricular rate regularization pacing, atrial anti-tachycardia pacing, atrial cardioversion therapy, or atrial defibrillation therapy.

Figure 3:
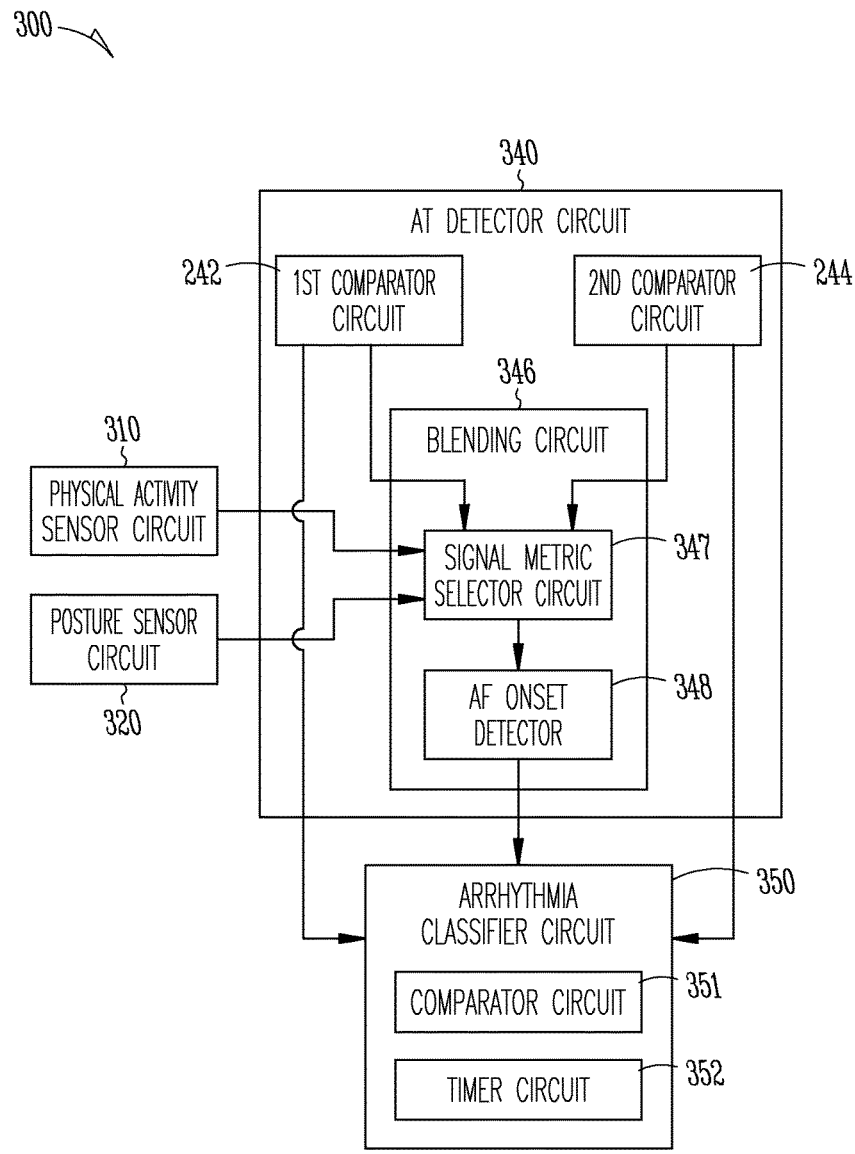
FIG. 3 illustrates generally another example of an AT detection circuit.

FIG. 3 illustrates generally an example of an AT detection circuit 300, which can be an embodiment of the HS-based AT detection circuit 200. The AT detection circuit 300 can include one or more of a physical activity sensor circuit 310, a posture sensor circuit 320, and an AT detector circuit 340. The AT detection circuit 300 can optionally include an arrhythmia classifier circuit 350.

The AT detector circuit 340 can be an embodiment of the AT detector circuit 240, and can be implemented as a part of a microprocessor circuit in the CRM system 100. The microprocessor circuit can be a dedicated processor or general purpose processor that can receive and execute a set of instructions of performing the functions, methods, or techniques described herein.

The physical activity sensor circuit 310 can be configured to detect a physical activity or exertion level of the patient. The activity sensor can be an implantable, wearable, or otherwise ambulatory sensor that is external to the patient or implanted inside the body. The activity sensor can be included in at least one part of an implantable system, such as an implantable device, or a lead coupled to the implantable device. In an example, the activity sensor can include a single-axis or multi-axis accelerometer configured to sense an acceleration signal of at least a portion of the subject's body. The strength of the acceleration signal can be indicative of the physical activity level. In another example, the activity sensor can include a respiratory sensor configured to measure respiratory parameters correlative or indicative of respiratory exchange, i.e., oxygen uptake and carbon dioxide output. Examples of the respiratory parameters can include respiration rate, tidal volume, minute ventilation, peak or trough of a respiration signal, or other indicators of respiration depth; descriptors of respiration pattern such as apnea index indicating the frequency of sleep apnea, hypopnea index indicating the frequency of sleep hypopnea, apnea-hypopnea index (AHI) indicating the frequency of or sleep hypopnea events, or a rapid shallow breathing index (RSBI) computed as a ratio of respiratory frequency (number of breaths per minutes) to tidal volume, among other respiratory parameters.

The posture sensor circuit 320 can be configured to detect a posture or position of the patient. Examples of the posture sensor can include a tilt switch, a single axis accelerometer, or a multi-axis accelerometer, among others. The posture sensor can be disposed external to the body or implanted inside the body. Posture can be represented by, for example, a tilt angle. In another example, patient posture or physical activity information can be derived from thoracic impedance information, such as by clustering the thoracic impedance information, as described by Thakur et al., in U.S. Patent Application No. 61/423,128, entitled "POSTURE DETECTION USING THORACIC IMPEDANCE", which is herein incorporated by reference in its entirety.

The AT detector circuit 340 can detect an AT event, such as an AF event, using signal metrics selected based on information about the patient physical activity level provided by the physical activity sensor circuit 310, or information about patient position or posture provided by the posture sensor circuit 320. Similar to the AT detector circuit 240, the AT detector circuit 340 can include a first comparator circuit 242 that can produce an atrial rhythm indicator such as by comparing the CLV values to a CLV threshold ($CLV_{TH}$), and a second comparator circuit 244 that can produce an atrial kick indicator such as such as by comparing a S4 heart sound intensity to a specified criterion.

The blending circuit 346 can include a signal metric selector circuit 347 coupled to the first and second comparator circuits and one or both of the physical activity sensor circuit 310 or a posture sensor circuit 320. In an example, the blending circuit 346 can select one of the detected atrial electrical activation (such as provided by the first comparator circuit 242) or the detected S4 heart sounds (such as provided by the second comparator circuit 244) for use in detecting the AF event based on information about the patient's activity or exertion level such as provided by the physical activity sensor circuit 310. The present inventors have recognized that a HS sensor may be more susceptible to noise or interference such as motion artifacts, thus becomes less reliable when the patent is physically active e.g., during physical exercise) than when the patient is less active (e.g., during a rest or sleep state). By contrast, cardiac electrical signals, such as the ECG or the EGMs, may be less susceptible to motion artifacts. The signal metric selector circuit 347 can select the detected atrial electrical activation (e.g., P waves from the ECG or atrial sensing events from the atrial EGM) or an atrial rhythm indicator (e.g., the CLV calculated using the HRs or CLs obtained from the ECG or the EGM) if the patient's physical activity level exceeds a specified activity threshold indicating the patient being physically active. The signal metric selector circuit 347 can select S4 intensity, either alone or together with the atrial electrical activation or the atrial rhythm indicator if the physical activity level falls below the specified activity threshold indicating the patient being physically inactive, resting or sleeping. In another example, the signal metric selector circuit 347 can select the detected atrial electrical activation or the atrial rhythm indicator in response to the posture sensor circuit 320 detecting a first posture, or select S4 intensity if the posture sensor circuit 320 detecting a second posture different from the first posture. By way of non-limiting example, the first posture can include an upright or standing position or posture, and the second posture can include a recumbent, supine, or lying down position or posture.

Additionally or alternatively, the signal metric selector circuit 347 can include a signal quality analyzer circuit coupled to the posture sensor circuit 320. The signal quality analyzer can compute a first signal quality indicator of the detected atrial electrical activation occurring during the detected posture, and a second signal quality indicator of the detected S4 heart sound occurring during the detected posture. The first signal quality indicator can include a signal to noise ratio of the detected atrial electrical activation ($SNR_E$) during the detected posture, and a second signal quality indicator includes a signal to noise ratio of the detected S4 heart sound ($SNR_{S4}$) during the detected posture. The signal metric selector circuit 347 can select the detected atrial electrical activation if the first signal quality indicator is greater than the second signal quality indicator by a specified margin, or select the S4 heart sound if the second signal quality is great than the first signal quality indicator by a specified margin.

The AF onset detector 348, coupled to the signal metric selector circuit 347, can use the selected signal metric to detect the AF event, such as in response to non-detection of P waves, CLV exceeding the threshold $CLV_{TH}$, or non-detection of S4 heart sound or the S4 intensity falling below the threshold $\|S4\|_{TH}$.

The arrhythmia classifier circuit 350 can be coupled to AT detector circuit 340, and the first and second signal metric generator circuits 242 and 244 or the memory circuit 230, and configured to classify the detected AT event as one of an AF event or an atrial flutter (AFL) event. An AFL occurs when an abnormal conduction circuit develops inside the atrium and drives the atrial rate excessively fast, such as approximately 250-300 beats per minute. Compared to typically discoordinated atrial activity during AF, electrical activity in the atria during AFL may be coordinated.

The arrhythmia classifier circuit 350 can determine a composite metric using the cardiac electrical signal metric and the HS metric. The arrhythmia classifier circuit 350 can confirm the detected AT event as an AF event if the composite metric meets a first specified criterion, or classify the detected AT event as an AFL event if the composite metric meets a second specified criterion. In an example, the arrhythmia classifier circuit 350 can include a comparator circuit 351 that can generate an atrio-ventricular (A-V) conduction pattern representing a correspondence between atrial and ventricular activities. The A-V conduction pattern can include a ratio (AVR) of a number of S4 heart sounds to a number of ventricular activations during a specified number of cardiac cycles. For example, the AVR can be represented by n:1 A-V conduction indicating a correspondence of n atrial contractions (e.g., n S4 heart sounds) for every one ventricular activation (e.g., an R wave or a QRS complex in a ECG, or a ventricular sensing event in an EGM). The AVR can be represented by n:m A-V conduction indicating a correspondence of n atrial contractions (e.g., n S4 heart sounds) for every m ventricular activations. The arrhythmia classifier circuit 350 can determine a composite metric including a variability measure ($AVR_{var}$ of the AVR, such as a range, variance, standard deviation, or other statistics of spreadness that indicate consistency of the AV conduction pattern over time. The arrhythmia classifier circuit 350 can confirm the detected AT event as an AF event if the $AVR_{var}$ exceeds a specified threshold, which indicates lack of a consistent A-V conduction pattern. The arrhythmia classifier circuit 350 can classify the detected AT event as an AFL event if the $AVR_{var}$ falls below the specified threshold, which indicates a consistent A-V conduction pattern.

In an example, the arrhythmia classifier circuit 350 can include a timer circuit 352 that can generate an atrio-ventricular (A-V) conduction delay, which can include a time interval between the detected S4 heart sound and the ventricular activation (e.g., R waves, QRS complexes in an ECG, or ventricular sensed events in an EGM) within the same cardiac cycle. A consistent and stable atrio-ventricular interval (AVI) may indicate occurrence of an AFL event, while an inconsistent and variable AVI may be a characteristic of an AF event. The arrhythmia classifier circuit 350 can determine a composite metric including a variability measure ($AVI_{var}$) of the AVI, such as a range, variance, standard deviation, or other statistics of spreadness that indicate consistency of the AV conduction delay over time. The arrhythmia classifier circuit 350 can confirm the detected AT event as an AF event if the $AVI_{var}$ exceeds a specified threshold, or classify the detected AT event as an AFL event if the $AVI_{var}$ falls below the specified threshold.

Figure 4:
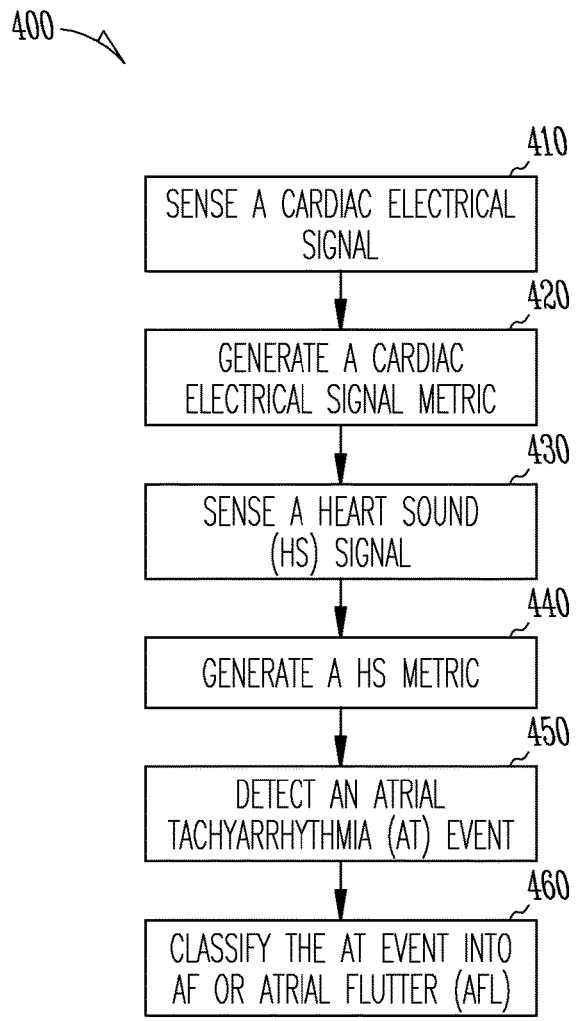
FIG. 4 illustrates generally an example of a method for detecting an AT event in a patient.

FIG. 4 illustrates generally an example of a method 400 for detecting an AT event in a patient. An example of the AT event is an atrial fibrillation (AF) event. The method 400 can be implemented and operate in an ambulatory medical device or in a remote patient management system. In an example, the IMD 110 or the external system 120, including its various examples discussed in this document, can be programmed to perform method 400, including its various examples discussed in this document.

The method 400 can begin at 410 where a cardiac electrical signal can be sensed, such as by using one or more implantable, wearable, or otherwise ambulatory cardiac activity sensors configured to sense cardiac electrical activity. Examples of the cardiac electrical signal can include surface or subcutaneous electrocardiogram (ECG), or one or more electrocardiograms (EGMs) sensed by using electrodes on one or more of the leads 108A-C or the can 112. Atrial depolarization events, such as P waves sensed from an ECG or atrial sensing events from an atrial EGM, and ventricular depolarization events, such as R waves sensed from an ECG or ventricular sensing events from a ventricular EGM, can be sensed.

At 420, one or more cardiac electrical signal metric can be generated. In one example, the cardiac electrical signal metric can include cycle length variability (CLV) or a heart rate variability (HRV) value indicative of variability of the CL or HR. The CLR or HRV can include a spreadness measure computed using a plurality of HRs or CLs over a specified period of time. In an example, the cardiac electrical signal metric can include a presence or intensity of the atrial depolarizations, such as a P wave or atrial sensing events.

At 430, a heart sound (HS) signal can be sensed, such as by using one or more physiologic sensors that can sense acoustic or mechanical vibration of a heart. Examples of the sensors for sensing HS can include an accelerometer, an acoustic sensor such as a microphone, piezo-based sensor, or other vibrational or acoustic sensors can also be used to sense the HS signal.

At 440, at least one HS metric can be generated from the sensed HS signal. The HS metric can be indicative or correlative of atrial mechanical contraction, which can include a S4 heart sound metric. The S4 heart sound may generally be associated with atrial contraction. Regular and forceful atrial contraction may be diminished during an AF episode. A detection of forceful S4 may be an evidence of absence of AF. The S4 heart sound can be detected using a specified detection window with reference to a physiologic event such as R wave, Q wave, or QRS complexes, or other HS components such as S1 or S3 heart sounds. The S4 heart sound can additionally or alternatively be detected using a S4 template matching method.

The S4 metric can include a detection status of S4 heart sound, and temporal, statistical, or morphological features of the detected S4 heart sound. Examples of the intensity of a HS component can include amplitude of a detected HS component in a time-domain HS signal, a transformed HS signal such as integrated HS energy signal, or in a frequency-domain HS signal such as the peak value of the power spectral density, or peak value of a generic measurement within the respective HS detection window, such as peak envelop signal or root-mean-squared value of the portion of the HS signal within the HS detection window.

At 450, the cardiac electrical signal metric and the HS metric can be used to detect an AT event, such as an AF event, such as by using the AT detector circuits 240 or 340 as illustrated in FIGS. 2-3, or a microprocessor that can be configured to receive and execute a set of instructions of performing the functions, methods, or techniques described herein. In an example, the cardiac electrical signal metrics, including one or more of a cycle length variability (CLV) of cycle length (CL) or HR computed from the cardiac electrical signal, or a detection of atrial electrical activation (e.g., P waves in a ECG), can be generated. HS metrics, including one or more of a S4 detection status indicating whether a S4 heart sound is detected within the cardiac cycle, or a S4 intensity indicator of the detected S4 heart sound, can also be generated. Detecting the AF event can include comparing the CLV to a CLV threshold ($CLV_{TH}$), and comparing the S4 intensity (if S4 is detected) to a S4 intensity threshold ($\|S4\|_{TH}$). An AF is deemed detected if (1) the CLV value exceeds a CLV threshold ($CLV_{TH}$), and (2) the S4 detection status indicates a non-detection of S4 heart sound, or the S4 intensity indicator falls below a S4 intensity threshold ($\|S4\|_{TH}$).

In an example, the $CLV_{TH}$ can be set a relatively low level such that CLV can be sensitive to cycle length variations produced by AF or other physiologic or non-physiological conditions. The $\|S4\|_{TH}$ can be selected such that the atrial kick indicator, such as a non-detection of S4 or a below-the-threshold S4 intensity can be specific to an AF event. Other examples of detecting AF are discussed below, such as with reference to FIGS. 5-8.

The method 400 can additionally include a step 460 of classifying the detected AT event as one of an AF event or an atrial flutter (AFL) event, such as by using the arrhythmia classifier circuit 350 or any variants thereof. A composite metric can be determined using the cardiac electrical signal metric and the HS metric. In an example, the composite metric can include an atrio-ventricular (A-V) conduction pattern representing a pattern of correspondence between atrial and ventricular activities. The A-V conduction pattern can include a ratio (AVR) of a number of S4 heart sounds to a number of ventricular activations during a specified number of cardiac cycles. In another example, the composite metric can include an A-V conduction delay, such as a time interval (AVI) between the detected S4 heart sound and the ventricular activation within the same cardiac cycle. A variability measure ($AVR_{var}$) of the AVR, or a variability measure ($AVI_{var}$) of the AVI, can be computed, which respectively represents consistency of the atrio-ventricular conduction pattern or stability of the atrio-ventricular interval. An AF event can be confirmed if the $AVR_{var}$ or the $AVI_{var}$ exceeds respective thresholds, indicating a consistent atrio-ventricular conduction pattern or a stable atrio-ventricular interval. Alternatively, the detected AT event can be classified as an AFL event if the $AVR_{var}$ or the $AVI_{var}$ falls below the respective thresholds, indicating an inconsistent atrio-ventricular conduction pattern or an unstable atrio-ventricular interval.

The method 400 can include a step of generating an alert of a detection of an AF event or AFL event. The method 400 can include a step of delivering a specified therapy to the patient, such as by using a therapy circuit in response to a detection of the AF or AFL event, or to withhold the therapy in response to a detection of termination of the AF or the AFL event. The therapy can include one or more of a cardiac stimulation therapy, a cardiac ablation therapy, a neurostimulation therapy, or pharmacological therapy. In an example, the cardiac stimulation therapy can be in a form of electrostimulation to a target inside or on the heart, including an endocardium or an epicedium of an atrium or a ventricle.

Figure 5A:
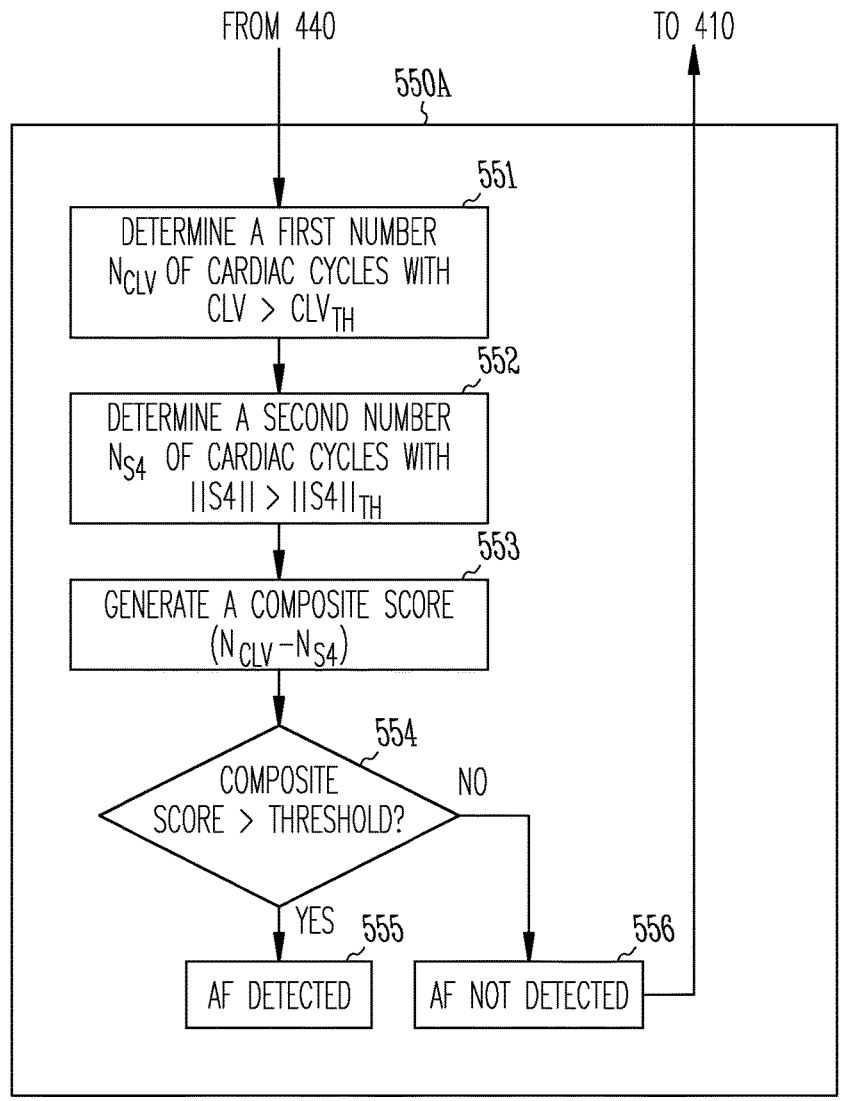
FIGS. 5A-B illustrate generally examples of methods for detecting an AF event using a cardiac electrical signal metric and a HS metric.
Figure 5B:
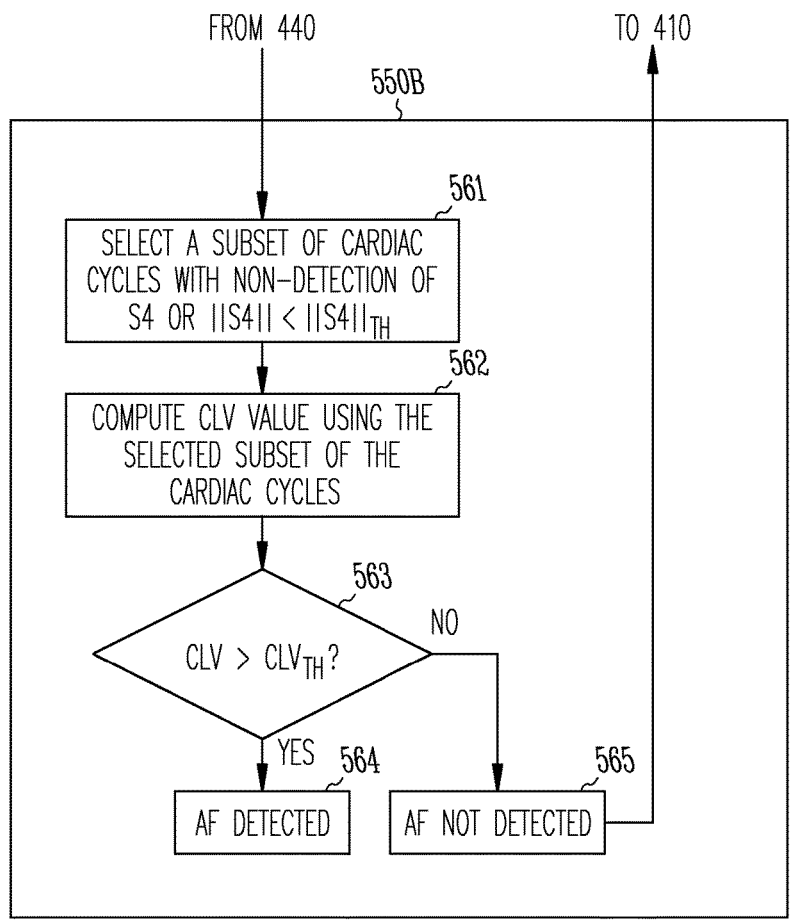

FIGS. 5A-B illustrate generally examples of methods for detecting an AF event using a cardiac electrical signal metric and a HS metric. FIG. 5A illustrates a method 550A, and FIG. 5B illustrates a method 550B, each of which can be an embodiment of the step 450 of the method 400 as illustrated in FIG. 4.

The method 550A includes a step at 551 for determining, from a plurality of CLV values computed over a plurality of cardiac cycles, a first subset of CLV values each exceeding the $CLV_{TH}$. A first relative number ($N_{CLV}$) can also be determined, such as a ratio, a fraction, or a percentage of the number of CLV values in the first subset to the total number of the plurality of the CLV values. At 552, from the plurality of cardiac cycles used for computing the CLV values, a second subset of cardiac cycles can be determined, where each cardiac cycle in the second subset includes a detected S4 heart sound with corresponding S4 intensity exceeding the threshold $\|S4\|_{TH}$. A second relative number ($N_{S4}$) can also be determined, such as a ratio, a fraction, or a percentage of the number of cardiac cycles in the second subset to the total number of the plurality of the CLV values. In an example, the $N_{CLV}$ can represent percentage of the plurality of cardiac cycles satisfying $CLV > CLV_{TH}$, and $N_{S4}$ can represent percentage of the plurality of cardiac cycles satisfying $\|S4\| > \|S4'\|_{TH}$. At 553, a composite score can be generated using the first and second relative number, such as a difference $N_{CLV} - N_{S4}$. A larger $N_{CLV}$ indicates higher likelihood of occurrence of an AF event, and a larger $N_{S4}$ is an evidence of forceful atrial contraction and thus lower likelihood of occurrence of an AF event. As such, the difference ($N_{CLV} - N_{S4}$) can be used as a cumulative evidence of occurrence of an AF event. At 554, the composite score can be compared against a criterion, such as a threshold value. An AF event is deemed detected at 555 if the composite score exceeds the threshold. If the composite score does not exceed the threshold, then at 556 no AF event is deemed detected; and the detection process can be continued by sensing cardiac electrical signals at 410.

The method 550B includes a step 561 of selecting, from a plurality of cardiac cycles for detecting S4 heart sound, a subset of cardiac cycles each having the S4 detection status indicating non-detection of S4 heart sound within the corresponding cardiac cycle, or the S4 intensity indicator of the detected S4 heart sounds falling below the $\|S4\|_{TH}$, that is, $\|S4\| < \|S4\|_{TH}$. The selected cardiac cycles thus represent time intervals free of forceful atrial kick, an indication of presence of AF. At 562, only the selected subset of the cardiac cycles are used to compute a CLV value, such as a variance, a standard deviation, or other statistical measure of spreadness of the selected cardiac cycles. At 563, the CLV can be compared to a threshold $CLV_{TH}$. If the CLV value exceeds the threshold $CLV_{TH}$, an AF event is deemed detected at 564. If the CLV value falls below the $CLV_{TH}$, then no AF event is deemed detected at 565; and the detection process can be continued by sensing cardiac electrical signals at 410.

Figure 6:
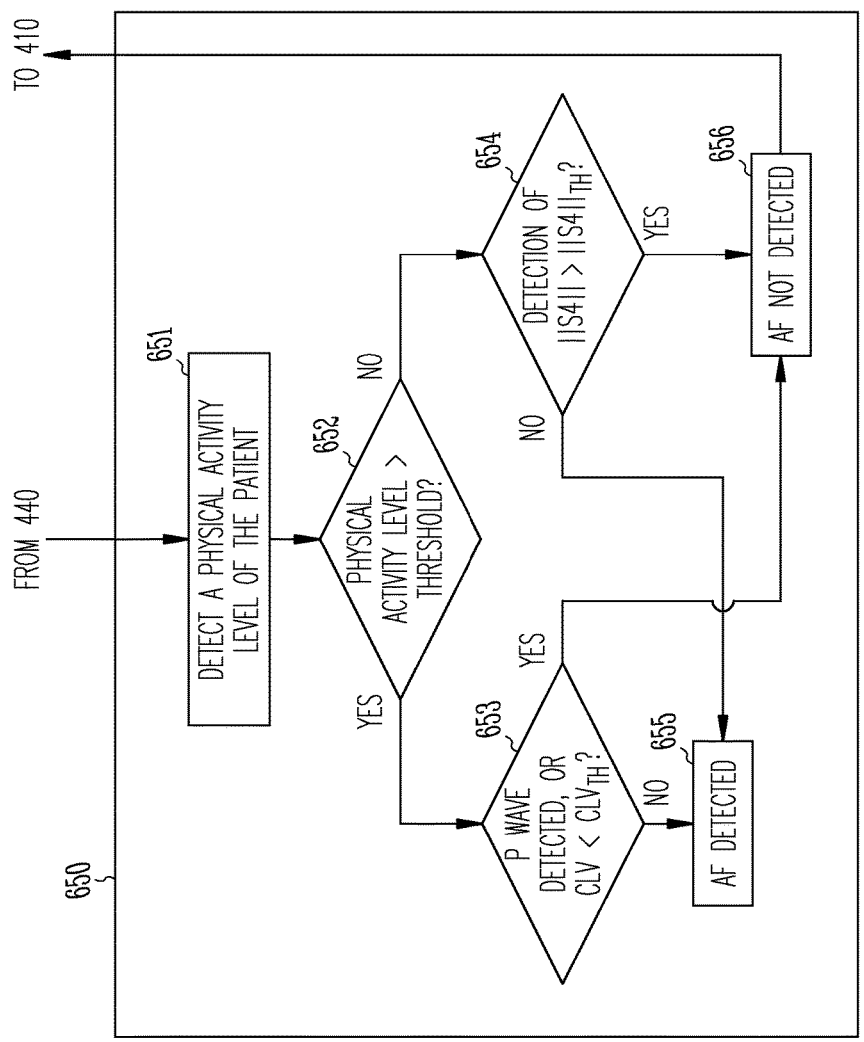
FIG. 6 illustrates generally an example of a method for detecting an AF event using a cardiac electrical signal, a HS signal, and information about physical activity level of the patient.

FIG. 6 illustrates generally an example of a method 650 for detecting an AF event using a cardiac electrical signal, a HS signal, and information about physical activity level of the patient. The method 650 can be an embodiment of the step 450 of the method 400 as illustrated in FIG. 4, and can be programmed to and executed by the AT detection circuit 300. The method 650 can include a step 651 of detecting a physical activity or exertion level of the patient, such as by using a single-axis or multi-axis accelerometer or an impedance signal indicative of respiratory exchange. The strength of the acceleration signal, or the respiration rate, tidal volume, or minute ventilation, apnea-hypopnea index (AHI), a rapid shallow breathing index (RSBI), among other parameters derived from the respiration signal, can indicate the level of physical activity or exertion of the patient.

At 652, the detected physical activity or exertion level can be compared to a threshold. If the physical activity level exceeds the threshold, such as when the patient is physically active or during exercise, then the detected cardiac electrical activation (such as the P waves or the CLV values) can be used for detecting AF event at 653. For example, as illustrated in FIG. 6, if P waves are detected or the CLV value falls below the threshold $CLV_{TH}$, no AF event is deemed detected at 656. However, if at 653 the P waves are not detected, and if the CLV is greater than the $CLV_{TH}$, an AF event is deemed detected at 655. If at 652 the patient's physical activity or exertion level is less than the activity threshold, such as when the patient is physically inactive or in a state of rest or sleep, the HS metric such as the S4 heart sound metric can be used to detect the AF event. At 654, the S4 intensity indicator can be compared to the threshold $\|S4\|_{TH}$. If the S4 intensity exceeds the $\|S4\|_{TH}$, forceful atrial kick is likely present and no AF event is deemed detected at 656. However, if the S4 intensity falls below the $\|S4\|_{TH}$, or no S4 heart sound is detected, then an AF event is deemed detected at 655. When no AF event is detected either according to the electrical signal metrics or the HS metric, the detection process can be continued by sensing cardiac electrical signals at 410.

Figure 7:
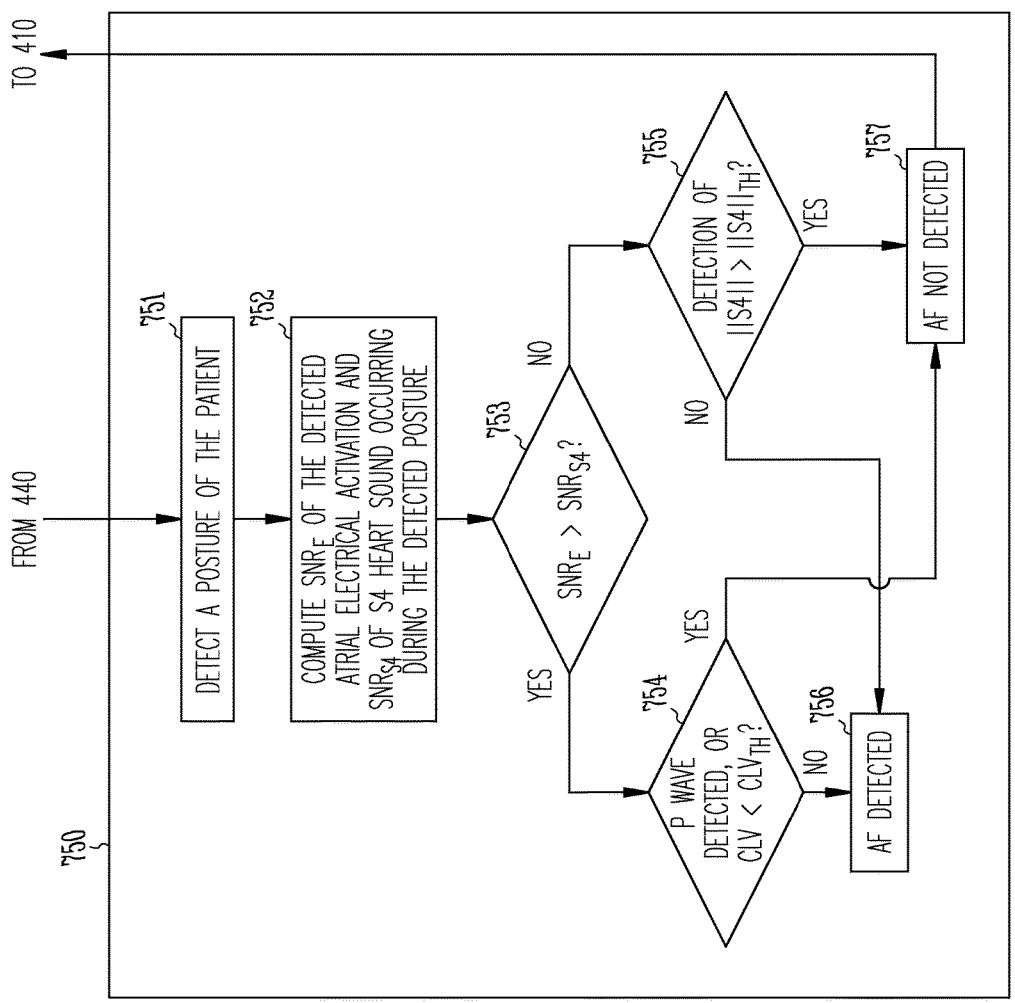
FIG. 7 illustrates generally an example of a method for detecting an AF event using a cardiac electrical signal, a HS signal, and posture information.

FIG. 7 illustrates generally an example of a method 750 for detecting an AF event using a cardiac electrical signal, a HS signal, and posture information. The method 750 can be an embodiment of the step 450 of the method 400 as illustrated in FIG. 4. The method 750 can include a step 751 of detecting the patient's posture, such as by using a tilt switch, a single axis accelerometer, or a multi-axis accelerometer, thoracic impedance sensors, among others. At 752, respective signal quality indicators of the detected atrial electrical activation and the S4 heart sound can be determined, such as a first signal-to-noise ratio (SNR) of the detected atrial electrical activation occurring during the detected posture, and a second signal-to-noise ratio ($SNR_{S4}$) of the detected S4 heart sound occurring during the detected posture. The two signal quality indicators can be compared at 753. If $SNR_E$ is greater than $SNR_{S4}$, the electrical signal metrics are deemed more reliable than S4 metric, and the cardiac electrical activation (such as the P waves or the CLV values) can be used for detecting AF event at 754. Similar to step 653 of FIG. 6, an AF event is deemed not detected at 757 if the P wave is detected or the CLV<$CLV_{TH}$, or otherwise deemed detected at 756. If at 753 the $SNR_E$ is less than $SNR_{S4}$, the HS metric is deemed more reliable than cardiac electrical signal metrics, and the S4 intensity can be used to detect the AF event at 755. An AF event is deemed not detected at if $\|S4\|>\|S4'\|_{TH}$, or otherwise deemed detected at 756. When no AF event is detected either according to the electrical signal metrics or the HS metric, the detection process can be continued by sensing cardiac electrical signals at 410.

Figure 8:
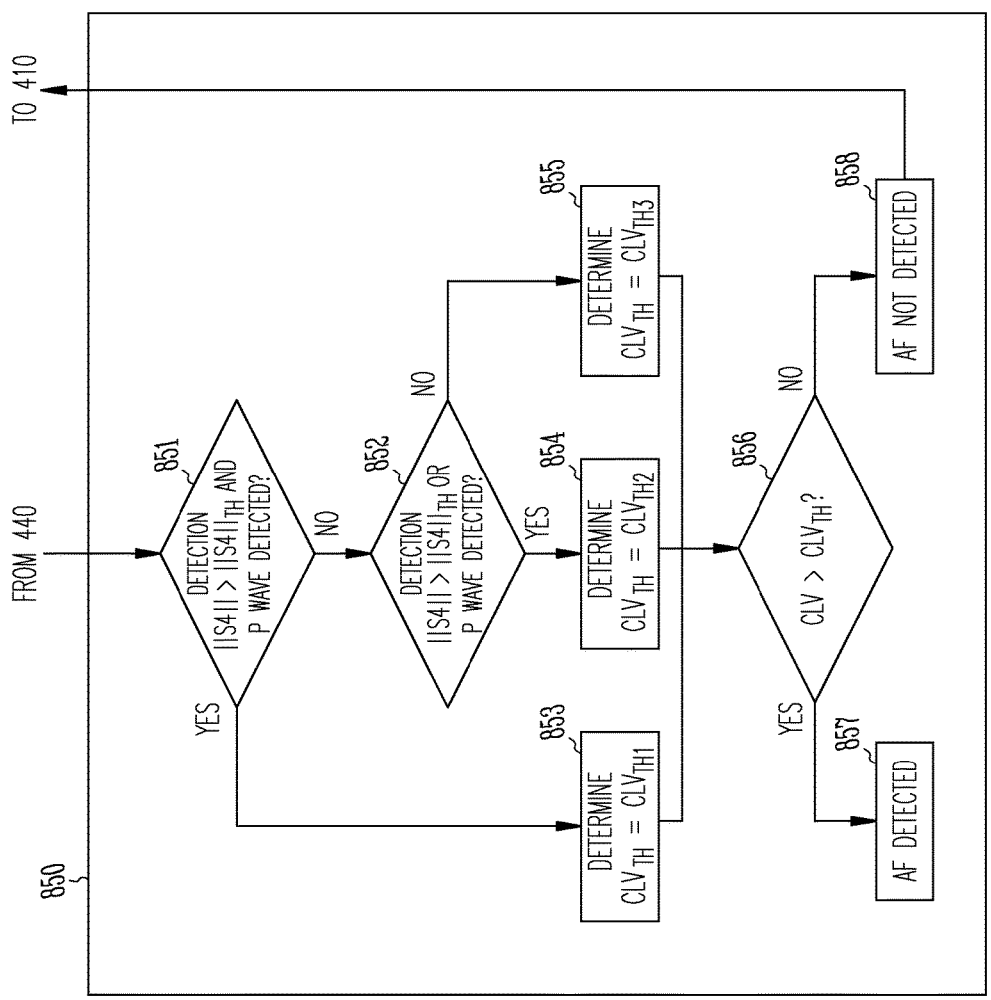
FIG. 8 illustrates generally another example of a method for detecting an AF event using a cardiac electrical signal and a HS signal.

FIG. 8 illustrates generally an example of a method 850 for detecting an AF event using a cardiac electrical signal and a HS signal. The method 850 detects an AF event if the CLV value exceeds a CLV threshold ($CLV_{TH}$), where the threshold $CLV_{TH}$ can be determined using at least one of the detected atrial electrical activation (e.g., P waves or atrial sensing events) and the atrial kick indicator (e.g., a detected S4 with intensity exceeding a threshold $\|S4\|_{TH}$). If the detected S4 intensity exceeds the threshold value $\|S4\|_{TH}$ and the P waves are detected at 851, then a first CLV threshold ($CLV_{TH1}$) can be determined at 853. If only one, but not both, of the atrial electrical activation and atrial kick indicator are present, that is, either the P waves are detected or $\|S4\|>\|S4\|_{TH}$ at 852, then a second threshold ($CLV_{TH2}$) can be generated at 854. If there is neither a detection of S4 heart sound (or the detected S4 intensity falls below the threshold $\|S4\|_{TH}$) nor a detection of atrial electrical activation (e.g., no P waves detected), then a third threshold ($CLV_{TH3}$) can be generated at 855. A detection of $\|S4\|>\|S4\|_{TH}$ along with the detection of P waves provides a stronger evidence of presence of an AF episode than either $\|S4\|>\|S4\|_{TH}$ or the detection of P waves alone, and a non-detection of S4 heart sound along with a non-detection of P waves is highly predictive of presence of an AF episode. The CLV thresholds can thus be determined such that $CLV_{TH1}>CLV_{TH2}>CLV_{TH2}$ to avoid false positive detection of AF event (with a large $CLV_{TH1}$) or to avoid missing a detection of a true AF event (with a small $CLV_{TH3}$). In some examples, when the condition at 852 is met, atrial kick indicator may provide different levels of evidence of occurrence of AF than a detection of atrial electrical activation, and different CLV threshold values may be determined in accordance with the detection of $\|S4\|>\|S4\|_{TH}$ or the detection of P waves, instead of a common threshold $CLV_{TH2}$. For example, based on population data, empirical knowledge, or signal quality (such as a signal noise ratio), if $\|S4\|>\|S4\|_{TH}$ is found to more predictive of an occurrence of an AF event than detection of P waves, the CLV threshold ($CLV_{TH2a}$) corresponding to $\|S4\|>\|S4\|_{TH}$ (but no P wave detection) can be higher than the CLV threshold ($CLV_{TH2b}$) corresponding to P wave detection (but no detection of S4 or $\|S4\|<\|S4\|_{TH}$). The CLV threshold values under different combinations of atrial electrical activation and atrial kick indicator can be related as $CLV_{TH1}>CLV_{TH2a}>CLV_{TH2b}>CLV_{TH3}$.

At 856, the CLV can be compared to the threshold $CLV_{TH}$. If the CLV value exceeds a CLV threshold $CLV_{TH}$, an AF event is deemed detected at 857. If the CLV value falls below the $CLV_{TH}$, then no AF event is deemed detected at 858; and the detection process can be continued by sensing cardiac electrical signals at 410.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it wilt not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
   a first signal metric generator circuit configured to determine a cycle length variability (CLV) over measurements of multiple cardiac cycles from a patient;
   a second signal metric generator circuit configured to generate an S4 heart sound metric indicative or correlative of atrial mechanical contraction using heart sound information of the patient; and
   an atrial tachyarrhythmia (AT) detector circuit configured to detect an AT event of the patient using the determined CLV and the generated S4 heart sound metric.

2. The system of claim 1, wherein the AT event includes an atrial fibrillation (AF), wherein the S4 heart sound metric includes an S4 detection status indicating whether an S4 heart sound is detected within a cardiac cycle, and wherein the AT detector circuit is configured to detect AF of the patient using the determined CLV and the S4 detection status indicating a non-detection of the S4 heart sound within the cardiac cycle.

3. The system of claim 1, wherein the S4 heart sound metric includes an S4 detection status indicating whether an S4 heart sound is detected within a cardiac cycle or an S4 intensity indicator indicative of an intensity of a detected S4 heart sound, and wherein the AT detector circuit includes:
   a first comparator circuit configured to compare the CLV value to a CLV threshold ($CLV_{TH}$);
   a second comparator circuit configured to compare the S4 intensity indicator of the detected S4 heart sound to an S4 intensity threshold ($\|S4\|_{TH}$); and
   a blending circuit configured to detect the AF event if (1) the CLV value exceeds the $CLV_{TH}$, and (2) the S4 detection status indicates a non-detection of S4 heart sound, or the S4 intensity indicator falls below the $\|S4\|_{TH}$.

4. The system of claim 1, wherein the S4 heart sound metric includes an S4 intensity indicator indicative of an intensity of a detected S4 heart sound, and wherein the AT detector circuit includes:
   a first counter circuit configured to determine a first relative number of a first subset of a plurality of CLV values computed over a plurality of cardiac cycles, each CLV within the first subset exceeding a CLV threshold;
   a second counter circuit configured to determine a second relative number of a second subset of the plurality of cardiac cycles, each cardiac cycle within the second subset including a detected S4 heart sound with a corresponding S4 intensity indicator exceeding an S4 intensity threshold; and
   a blending circuit configured to generate a composite score using the first and second relative numbers, and detect the AF event if the composite score meets a specified criterion.

5. The system of claim 1, further comprising a beat selector circuit coupled to the second signal metric generator circuit, the beat selector circuit configured to select, from a plurality of cardiac cycles for detecting S4 heart sound, a subset of cardiac cycles each having an S4 heart sound metric including an S4 detection status indicating non-detection of the S4 heart sound within the corresponding cardiac cycle, or an S4 intensity indicator indicative of an intensity of a detected S4 heart sound falling below an S4 intensity threshold,
   wherein the first signal metric generator circuit is configured to compute the CLV value using the selected subset of the cardiac cycles; and
   wherein the AT detector circuit is configured to detect the AF event if the CLV value exceeds a CLV threshold.

6. The system of claim 1, further comprising a beat selector circuit coupled to the first signal metric generator circuit, the beat selector circuit configured to select from a plurality of cardiac cycles a subset of cardiac cycles corresponding to the CLV exceeding a CLV threshold,
   wherein the second signal metric generator circuit is configured to detect S4 heart sounds within the selected subset of the cardiac cycles and generate an S4 detection status indicating whether an S4 heart sound is detected within the selected subset of the cardiac cycles; and
   wherein the AT detector circuit is configured to detect the AF event if the S4 detection status indicating non-detection of the S4 heart sound within the selected subset of the cardiac cycles, or the S4 intensity indicator falling below an S4 intensity threshold.

7. The system of claim 1, wherein the S4 heart sound metric includes an S4 detection status indicating whether an S4 heart sound is detected within a cardiac cycle, the system further comprising:
   an activity sensor circuit configured to detect a physical activity level of the patient, wherein the AT detector circuit is configured to:
     detect the AF event using an atrial electrical activation if the detected physical activity level exceeds a specified activity threshold; or
     detect the AF event using the detected S4 heart sound if the detected physical activity level falls below the specified activity threshold.

8. The system of claim 1, wherein the S4 heart sound metric includes an S4 detection status indicating whether an S4 heart sound is detected within a cardiac cycle, the system further comprising:
   a posture sensor circuit configured to detect a posture of the patient, wherein the AT detector circuit is configured to:
     detect the AF event using an atrial electrical activation if the detected posture is a first posture; or detect the AF event using the detected S4 heart sound if the detected posture is a different second posture.

9. The system of claim 1, wherein the AT detector circuit is configured to detect the AF event if the CLV value exceeds a CLV threshold ($CLV_{TH}$), wherein the $CLV_{TH}$ is determined using the determined S4 heart sound metric.

10. The system of claim 9, wherein the S4 heart sound metric includes an S4 detection status indicating whether an S4 heart sound is detected within a cardiac cycle, and wherein the AT detector circuit is configured to:
 determine a first CLV threshold ($CLV_{TH1}$) in response to both of a detection of the S4 heart sound and a detection of an atrial electrical activation;
 determine a second CLV threshold ($CLV_{TH2}$) in response to one of a detection of the S4 heart sound or a detection of the atrial electrical activation; or
 determine a third CLV threshold ($CLV_{TH3}$) in response to neither a detection of the S4 heart sound nor a detection of the atrial electrical activation;
 wherein the $CLV_{TH1}$ is greater than the $CLV_{TH2}$, and the $CLV_{TH2}$ is greater than the $CLV_{TH3}$.

11. The system of claim 1, comprising an arrhythmia classifier circuit configured to
 classify the detected AT event as an atrial fibrillation (AF) event or an atrial flutter (AFL) event using the determined CLV and the generated S4 heart sound metric.

12. The system of claim 11, wherein the S4 heart sound metric includes an S4 detection status indicating whether an S4 heart sound is detected within a cardiac cycle, and wherein the determined CLV and the generated S4 heart sound metric includes a variability ($AVR_{var}$) of an atrio-ventricular conduction pattern including a ratio (AVR) of a number of detected S4 heart sounds to a number of ventricular activations during a specified number of cardiac cycles,
 wherein the arrhythmia classifier circuit is configured to classify the detected AT event as an AF event if the $AVR_{var}$ exceeds a specified threshold, or classify the detected AT event as an AFL event if the $AVR_{var}$ falls below the specified threshold.

13. The system of claim 11, wherein the determined CLV and the generated S4 heart sound metric includes a variability ($AVI_{var}$) of atrio-ventricular conduction delay including a time interval between the detected S4 heart sound and the ventricular activation within the same cardiac cycle, and
 wherein the arrhythmia classifier circuit is configured to classify the detected AT event as an AF event if the $AVI_{var}$ exceeds a specified threshold, or classify the detected AT event as an AFL event if the $AVI_{var}$ falls below the specified threshold.

14. A method, comprising:
 determining, using a first signal generator circuit, a cycle length variability (CLV) over multiple cardiac cycles from a patient,
 generating, using a second signal metric generating circuit, an S4 heart sound metric indicative or correlative of atrial mechanical contraction using heart sound information of the patient; and
 detecting, using an atrial tachyarrhythmia (AT) detector circuit, an AT event of the patient using the determined CLV and the generated S4 heart sound metric.

15. The method of claim 14, wherein:
 generating the S4 heart sound metric includes generating an S4 detection status indicating whether an S4 heart sound is detected within a cardiac cycle; and
 detecting the AT event includes detecting an atrial fibrillation (AF) event if (1) the CLV value exceeds a CLV threshold ($CLV_{TH}$), and (2) the S4 detection status indicates a non-detection of S4 heart sound.

16. The method of claim 15, wherein generating the S4 heart sound metric includes generating the S4 detection status or an S4 intensity indicator of the detected S4 heart sound, the method further comprising:
 determining a first relative number of a first subset of a plurality of CLV values computed over a plurality of cardiac cycles, each CLV within the first subset exceeding the $CLV_{TH}$;
 determining a second relative number of a second subset of the plurality of cardiac cycles, each cardiac cycle within the second subset including a detected S4 heart sound with a corresponding S4 intensity indicator exceeding the $\|S4\|_{TH}$; and
 generating a composite score using the first and second relative numbers,
 wherein detecting the AF event includes detecting the AF event if the composite score meets a specified criterion.

17. The method of claim 15, wherein generating the S4 heart sound metric includes generating the S4 detection status or an S4 intensity indicator of the detected S4 heart sound, the method further comprising:
 selecting, from a plurality of cardiac cycles for detecting the S4 heart sound, a subset of cardiac cycles each having the S4 detection status indicating non-detection of the S4 heart sound within the corresponding cardiac cycle, or the S4 intensity indicator falling below the $\|S4\|_{TH}$,
 wherein generating the CLV value includes computing the CLV using the selected subset of the cardiac cycles; and
 wherein detecting the AF event includes detecting the AF event if the CLV value exceeds the $CLV_{TH}$.

18. The method of claim 15, further comprising determining the $CLV_{TH}$ using the S4 heart sound, including:
 determining a first CLV threshold ($CLV_{TH1}$) in response to both of a detection of the S4 heart sound and a detection of an atrial electrical activation, a second CLV threshold ($CLV_{TH2}$) in response to one of a detection of the S4 heart sound or a detection of the atrial electrical activation, or a third CLV threshold ($CLV_{TH3}$) in response to neither a detection of the S4 heart sound nor a detection of the atrial electrical activation, wherein the $CLV_{TH1}$ is greater than the $CLV_{TH2}$, and the $CLV_{TH2}$ is greater than the $CLV_{TH3}$, and
 wherein detecting the AF event includes detecting the AF event if the CLV value exceeds the determined $CLV_{TH}$.

19. The method of claim 14, further comprising classifying the detected AT event as one of an atrial fibrillation (AF) event or an atrial flutter (AFL) event, including:
 determining a composite metric using ventricular activation from the patient and the S4 heart sound metric, the composite metric including one of more of an atrio-ventricular conduction pattern or an atrio-ventricular interval, and
 classifying the detected AT event as an AF event if the composite metric meets a first specified criterion indicating a consistent atrio-ventricular conduction pattern or a stable atrio-ventricular interval, or classifying the detected AT event as an AFL event if the composite metric meets a second specified criterion indicating an inconsistent atrio-ventricular conduction pattern or an unstable atrio-ventricular interval.

20. A system, comprising:
a first signal metric generator circuit configured to detect a ventricular activation from a patient;
a second signal metric generator circuit configured to detect an S4 heart sound from the patient; and
an atrial tachyarrhythmia (AT) detector circuit configured to:
  determine an atrioventricular conduction pattern or an atrioventricular conduction delay using the detected ventricular activation and the detected S4 heart sound; and
  detect an atrial arrhythmia as an atrial fibrillation event or an atrial flutter event using the determined atrioventricular conduction pattern or the atrioventricular conduction delay.

* * * * *